(12) United States Patent
Mugrage et al.

(10) Patent No.: US 7,501,439 B2
(45) Date of Patent: Mar. 10, 2009

(54) TARTRATE SALT OF ISOFAGOMINE AND METHODS OF USE

(75) Inventors: Benjamin Mugrage, Cranbury, NJ (US); Kamlesh A Sheth, Branchburg, NJ (US); David Palling, Montclair, NJ (US); Philip Rybczynski, Branchburg, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 11/752,658

(22) Filed: May 23, 2007

(65) Prior Publication Data

US 2007/0281975 A1    Dec. 6, 2007

Related U.S. Application Data

(60) Provisional application No. 60/890,719, filed on Feb. 20, 2007, provisional application No. 60/808,020, filed on May 24, 2006.

(51) Int. Cl.
*A61K 31/445*    (2006.01)

(52) U.S. Cl. .................................... 514/315; 546/242
(58) Field of Classification Search ................ 514/315; 546/242
See application file for complete search history.

(56) References Cited

U.S. PATENT DOCUMENTS

| 5,844,102 A | 12/1998 | Sierks et al. |
| 6,916,829 B2 | 7/2005 | Fan et al. |

OTHER PUBLICATIONS

Pandey, et al. "A general strategy towards the synthesis of 1-N-iminosugar type glycosidase inhibitors: demonstration by the synthesis of D- as well as L-glucose type iminosugars (isofagomines." 2000, vol. 41(45), pgas. 8821-8824.

*Primary Examiner*—Bernard Dentz
*Assistant Examiner*—David E Gallis
(74) *Attorney, Agent, or Firm*—Hoffmann & Baron, LLP

(57) ABSTRACT

A novel tartaric acid salt of Isofagomine (Isofagomine tartrate) that can be used for the treatment of Gaucher disease is provided. The invention also provides a crystalline form of isofagomine tartrate, method for preparing the salt, a pharmaceutical composition containing the salt, and a method of treating Gaucher disease.

9 Claims, 10 Drawing Sheets

TARTRATE SALT OF ISOFAGOMINE AND METHODS OF USE

CROSS-REFERENCED RELATED APPLICATIONS

This application claims priority from U.S. Provisional Patent Application Nos. 60/808,020, filed May 24, 2006, and 60/890,719, filed Feb. 20, 2007, both of which are incorporated by reference herein in their entirety.

BACKGROUND OF THE INVENTION

Gaucher disease is a lysosomal storage disorder that is associated with the accumulation of glycosphingolipids (GSL) in cells, particularly monocytes and macrophages, of afflicted individuals. This aberrant build up of GSL results from a genetic deficiency (mutation) in the gene encoding the lysosomal enzyme acid $\beta$-glucosidase (glucocerebrosidase; GCase), the lysosomal hydrolase that breaks down the GSL glucosylceramide (GluCer). The majority of glucocerebrosidase gene (Gba) mutations cause the GCase protein to misfold in the endoplasmic reticulum (ER). Misfolded GCase is recognized by the ER quality control system and subsequently degraded instead of being processed and trafficking to the lysosome.

Gaucher disease is pan-ethnic, with an overall disease frequency of about 1 in 50,000-100,000 births. Certain populations have a higher prevalence. In the Ashkenazi population, for example, about 1 in 15 people are carriers for a Gba mutation. According to the National Gaucher Foundation, about 2,500 Americans suffer from Gaucher disease.

Gaucher disease is an autosomal recessive disorder and is the most common lysosomal storage disease. The disease has been classified into three clinical types, depending on neurological involvement and disease severity. Type 1 is the most common and is characterized by an absence of neurological involvement. Patients exhibit a broad spectrum of severity; some can remain asymptomatic throughout life. Most Type 1 patients exhibit enlargement of the spleen and liver, skeletal abnormalities and bone lesions, and sustained inflammatory reactions. Hepatic glucocerebroside levels are elevated from 23-fold to 389-fold above normal levels in Type 1 Gaucher patients.

Type 2 Gaucher disease is the rarest and most severe form. It is associated with early onset of acute neurologic disease. The characteristic feature of neuronopathic Gaucher disease is an abnormality of horizontal gaze. Afflicted patients develop progressive encephalopathy and extrapyrimidal symptoms such as rigidity and Parkinson's-like movement (parkinsonism). Most Type 2 Gaucher patients die in early childhood from apnea or aspiration due to neurological deterioration.

Type 3 Gaucher disease also has neurological involvement, although to a lesser extent than Type 2. These patients also have the hepatosplenomegaly and skeletal defects characteristic of Type 1, as well as central nervous system symptoms that include poor coordination of movements (ataxia), seizures, paralysis of the eye muscles, epilepsy, and dementia. Patients with Type 3 Gaucher disease can live into adulthood, but may have a shortened life span. Three sub-classifications of Type 3 have been reported: Type 3a, which is associated with prominent hepatosplenomegaly and bone marrow disease; Type 3b, which is associated with limited systemic symptoms; and Type 3c, which is associated with hepatosplenomegaly, corneal opacities, progressive ataxia and dementia, and cardiac valve and aortic root calcification.

Approaches for the treatment of Gaucher disease include enzyme replacement therapy (ERT), bone marrow transplants (BMT), substrate reduction therapy (SRT), gene therapy, and pharmacological chaperone treatment. Isofagomine is a potent inhibitor of recombinant human acid $\beta$-glucosidase (GCase). Pharmacological chaperone methods for enhancing mutant enzyme activities in lysosomal storage disorders using enzyme inhibitors such as isofagomine are disclosed in commonly owned U.S. Pat. Nos. 6,916,829; 6,599,919; 6,589,964; 6,583,158, and 7,141,582 each of which are herein incorporated by reference in their entirety. For example, the addition of an inhibitor of GCase to a fibroblast culture medium has been shown to lead to an increase in the trafficking and lysosomal activity of GCase, indicating that such an inhibitor may be of therapeutic interest in the treatment of Gaucher disease.

It has recently been discovered that there is a link between mutations in the Gba gene and Parkinson's disease. In one study, a group of 17 patients with rare, early onset, treatment-resistant parkinsonism were found to have at least one allele with a Gba missense mutation, including homozygous and heterozygous individuals for N370S, a mutation typically associated with type 1, non-neuronopathic disease (Tayebi et al., Mol. Genet. Metab. 2003; 79; 104-109). In another study, a population of 99 Ashkenazi Jews with idiopathic Parkinson's disease were evaluated for six Gba mutations (N370S, L444P, 84GG, V394L, and R496H). Thirty-one Parkinson's patients had one or two mutant Gba alleles: 23 were heterozygous for N370S; 3 were homozygous for N370S; 4 were heterozygous for 84GG; and 1 was heterozygous for R496H (Aharon-Peretz et al., New Eng. J. Med. 2004; 351: 1972-77). The frequency of a mutant N370S allele was 5 times that among 1573 normal subjects, and that of 84GG was 21 times that of normal subjects. Among patients with Parkinson's disease, patients carrying a Gba mutation also were younger than those who were not carriers. This study suggests that heterozygosity for a Gba mutation may predispose Ashkenazi Jews to Parkinson's disease. Since isofagomine has been shown to cross the blood-brain barrier in animals, and increases the activity of both mutant wild-type GCase, it can be used to treat both Parkinson's patients who have a heterozygous mutation in GCase, or who are at risk for developing Parkinson's disease due to other factors, but who may benefit from increased levels of wild-type GCase.

Although the compound of isofagomine is a potent and selective recombinant human acid $\beta$-glucosidase (GCase) inhibitor, its use in pharmaceutical products presents challenges. For example, the hydrochloride salt of isofagomine (isofagomine-HCl) is disclosed in U.S. Pat. No. 5,844,102. However, isofagomine-HCl as well as isofagomine free base are not readily purified on a large scale and have poor solid state properties for use in an industrial scale manufacturing processes and pharmaceutical formulations.

SUMMARY OF THE INVENTION

In one embodiment, the present invention provides a compound of a tartaric acid salt of isofagomine or isofagomine tartrate, represented by the following chemical structure:

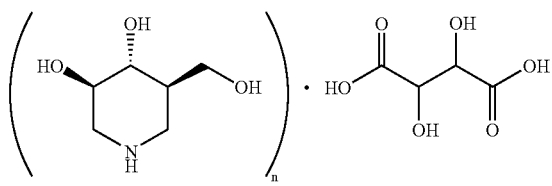

wherein n is 1 or 2. The invention also provides isofagomine tartrate with a high purity and in a crystalline form.

In another embodiment, the invention provides a composition containing isofagomine tartrate, preferably at least 50%, preferably, 90%, and even more preferably, 99%. The invention also provides a composition containing at least 90% or more of isofagomine tartrate where 90% of the isofagomine tartrate has a particle size of 1200 μm.

In other embodiment, the invention provides a pharmaceutical composition containing isofagomine tartrate and one or more pharmaceutically acceptable excipients.

In other embodiment, the invention provides a method for the preparation of an isofagomine tartrate. A method for preparing a highly purified isofagomine tartrate is also provided.

Yet, in another embodiment, the invention provides a method of treating Gaucher disease in a mammal by enhancing GCase activity in the mammal by administrating pharmaceutically effective amount of isofagomine tartrate or its pharmaceutical compositions.

In another embodiment, the invention provides L-(+)-tartaric acid salt of isofagomine. The invention also provides a complex of a tartaric acid and isofagomine.

In another embodiment, the invention provides a crystalline form of isofagomine tartrate. Preferably, the crystalline form has an x-ray powder diffraction pattern that includes five or more peaks of the following peaks: (2 theta) 9.29±0.009, 14.17±0.009, 16.34±0.009, 18.07±0.009, 18.72±0.009, 19.44±0.009, 20.56±0.009, 22.13±0.009, 23.01±0.009, 24.54±0.009, and 27.12±0.009. More preferably, the x-ray pattern includes the following peaks: (2 theta) 9.29, 14.17, 16.34, 18.07, 18.72, 19.44, 20.56, 22.13, 23.01, 24.54, and 27.12. Even more preferably, the crystalline form has an x-ray powder diffraction pattern that is substantially the same as the pattern shown in FIG. 5.

DETAILED DESCRIPTION

Figure 1:
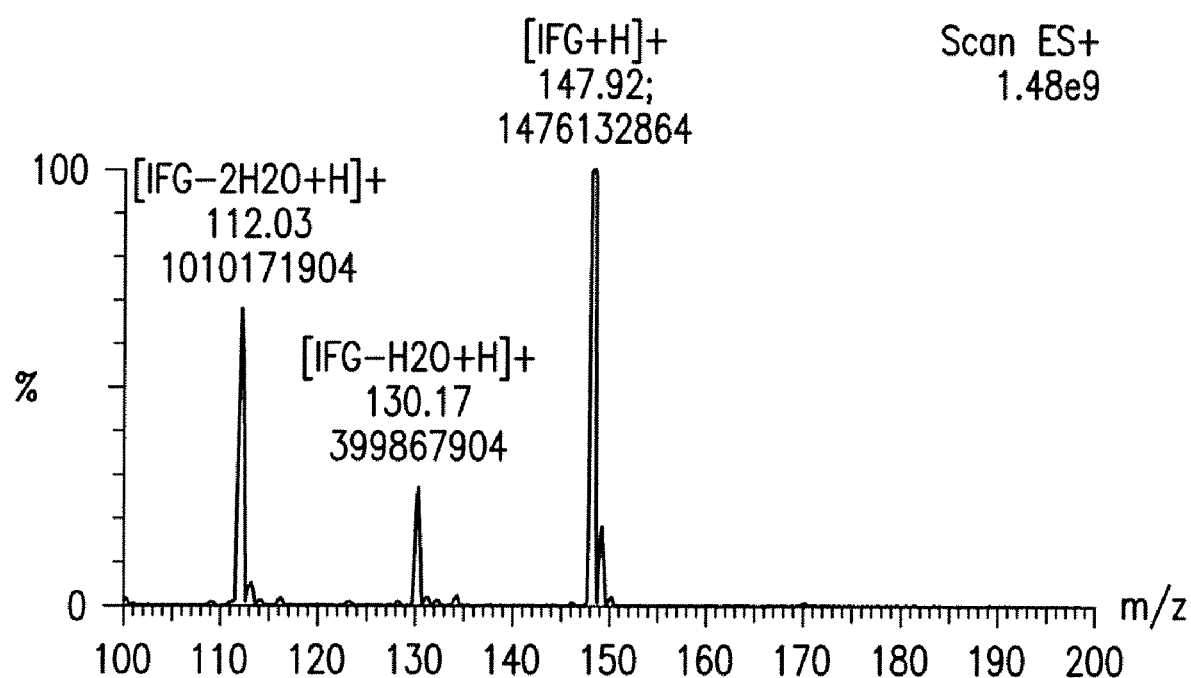
FIG. 1 shows a mass spectrum using positive ESI for isofagomine tartrate prepared according to one embodiment of the present invention.
Figure 2:
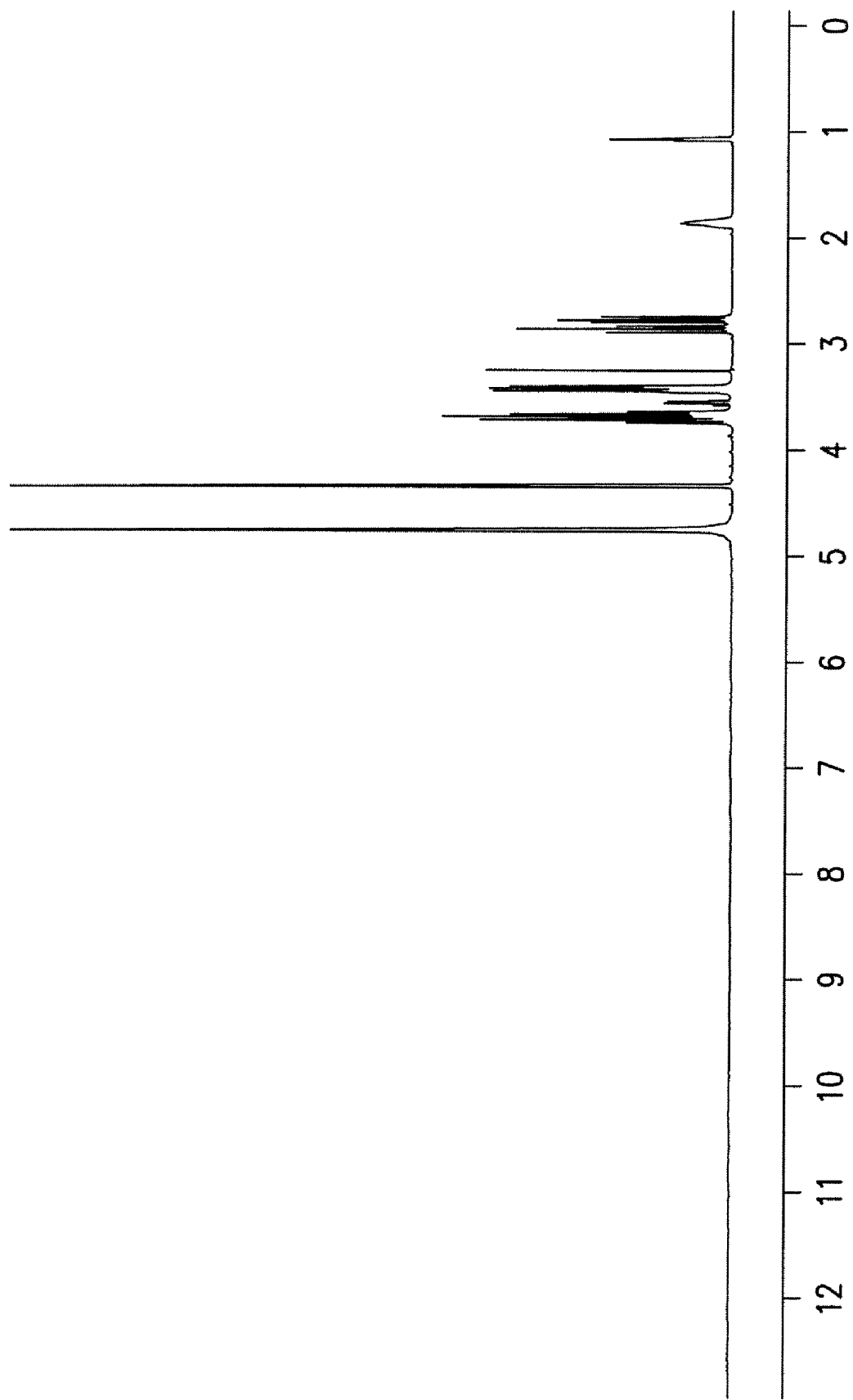
FIG. 2 shows an $^1$H NMR in $D_2O$ of isofagomine tartrate prepared according to one embodiment of the present invention.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention as well as how to make and use them.

The term "Gaucher disease" includes Type 1, Type 2 and Type 3 (including 3a, 3b and 3c), and intermediates and subgroups thereof based on phenotypic manifestations.

The terms "effective amount" and "amount effective" refer to the amount that is sufficient to result in a therapeutic response. A therapeutic response may be any response that a user (e.g., a clinician) will recognize as an effective response to the therapy, including improvements in the foregoing symptoms and surrogate clinical markers. Thus, a therapeutic response will generally be an amelioration of one or more symptoms of Gaucher disease, e.g., amelioration of progressive neurodegeneration in Types 2 and 3 Gaucher patients. The "therapeutically effective amount" will vary depending on the formulation used, the type of Gaucher disease and its severity, and the age, weight, physical condition and responsiveness of the mammal to be treated. A therapeutic response will also be an amelioration of one or more, symptoms of Parkinson's disease, or other α-synucleinopathies such as Lewy Body Dementia, for which isofagomine tartrate is contemplated for treatment.

The phrase "pharmaceutically acceptable" refers to molecular entities and compositions that are physiologically tolerable and do not typically produce untoward reactions at an unacceptable level when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" applied to pharmaceutical compositions of the invention refers to a diluent, excipient, or vehicle with which the Isofagomine tartrate is administered. The choice of carrier can be selected with regard to the intended route of administration and standard pharmaceutical practice. The pharmaceutical compositions may comprise as—or in addition to—the carrier any suitable binder(s), lubricant(s), suspending agent(s), coating agent(s), solubilizing agent(s). Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, and sesame oil. Suitable pharmaceutical carriers are described in "Remington's Pharmaceutical Sciences" by E. W. Martin, 18th Edition. In one particularly preferred embodiment of the present invention, the carrier is suitable for immediate-release, e.g., release of most or all of the active ingredient over a short period of time, such as 60 minutes or less, and make rapid absorption of the drug possible.

A "pharmaceutically acceptable carrier" means a carrier that is useful in preparing a pharmaceutical composition that is generally safe, non-toxic, and neither biologically nor otherwise undesirable, and includes an excipient that is acceptable for pharmaceutical use. A "pharmaceutically acceptable carrier" as used in the present application includes both one and more than one such carrier.

The term "hydroxyl protecting group" refers to any common protecting group for hydroxyl to avoid undesired reactions, such as, but not limited to, methoxymethyl, 4-methoxybenzyl, benzyl, dimethylisopropylsilyl, trimethylsilyl, and alkyl carbonyl.

"Individuals" refers to mammals, preferably humans, domestic animals, rodents or primates, and most preferably humans.

An "individual in need of treatment" is an individual that has developed, or is likely to develop, Gaucher disease or an α-synuclienopathy such as Parkinson's disease. In one embodiment, the individual is a member of the Ashkenazi Jewish population who has been diagnosed with or who has been identified as having an increased risk of developing Gaucher disease due to inherited mutations in the Gba gene. However, the term "individual" encompasses anyone in the world having, or genetically at risk of developing, Gaucher disease, or having at risk of developing an α-synucleinopathy such as Parkinson's disease.

As used herein, the term "enhancing" the activity GCase means stabilizing a conformation of a mutant GCase protein in the ER so that it i) folds in a conformation which permits it to exit the ER, resulting in increased levels of GCase in the ER, and/or ii) achieves its native location in the cell, and/or iii) exhibits catabolic activity towards cerebroside, its lipid substrate. This term also refers to increasing or prolonging the activity of an exogenously administered GCase protein, i.e., by increasing the stability and extending the in vivo half-life of GCase, thus, prolonging its activity.

The phrase "substantially pure," as used herein means that the isofagomine salt contains no more than about 5% of another compound. Preferably, the "substantially pure" isofagomine salt contains about 2% or less of any other compound. Even more preferably, the "substantially pure isofagomine salt contains about 1% or less of any other compound.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

As used herein, the singular forms "a," "an," and "the," include the plural unless the context clearly indicates otherwise. Thus, for example, reference "a" carrier includes one or more carriers.

In accordance with the present invention, a specific form of isofagomine, Isofagomine tartrate, is provided. Isofagomine tartrate has many improved characteristics compared with previously described forms of isofagomine. For example, isofagomine tartrate is more easily purifiable, especially in solvents such as water and/or ethanol, and has greater stability than other known salt forms of isofagomine. Isofagomine tartrate is particularly suitable for industrial scale production, e.g., production of greater than 1 Kg of product.

Isofagomine is (3R,4R,5R)-5-(hydroxymethyl)-3,4-piperidinediol having the following chemical structure:

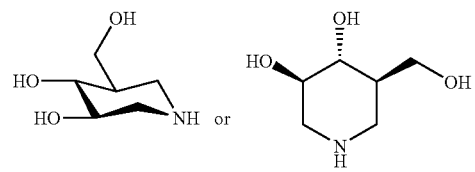

It has a molecular formula of $C_6H_{13}NO_3$ and a molecular weight of 147.17 g/mol. Synthesis of this compound is described in U.S. Pat. Nos. 5,844,102 to Sierks et al. and 5,863,903 to Lundgren et al. The '102 patent discloses that the compounds described therein can be combined with pharmaceutically acceptable salts, including salts of organic carboxylic acid salts such as acetic, lactic, tartaric, malic, isothionic, lactobionic, and succinic acids. However, the only salt exemplified in this patent (and in subsequent literature of which the applicant is aware) is the hydrochloride salt. As described herein, the hydrochloride salt is not suitable for industrial production or for formulation in dosage forms.

The term isofagomine tartrate used herein means a tartaric acid salt of isofagomine and can be represented as follows:

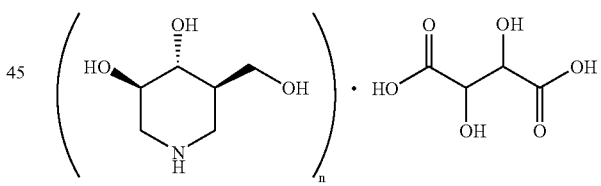

wherein n is 1 or 2. Tartaric acid could have different stereoisomeric forms; D- or L-tartaric acid, or DL- or meso-tartaric acid. The present invention, as well as Examples, is mainly described with reference to L-(+)-tartaric acid as a preferred embodiment and the isofagomine salt thereof. However, the term, tartaric acid is intended to cover both D and L isomers as well as a DL mixture and meso-tartaric acid, and thus the term isofagomine tartrate is intended to include mono- or di-isofagomine-L-tartrate, mono- or di-isofagomine-D-tartrate, mono- or di-isofagomine-DL-tartrate and/or mono- or di-isofagomine-meso-tartrate. L-tartaric acid is (2R,3R)-(+)-tartaric acid with enantiomer enrichment of 97% or higher, and D-tartaric acid is (2S,3S)-(−)-tartaric acid with enantiomer enrichment of 97% or higher. DL-tartaric acid is a mixture of D- and L-tartaric acid with enantiomer enrichment of less than 97%.

Isofagomine tartrate may be prepared from isofagomine free base dissolved in alcohol, preferably ethanol, and treated with the substituted carboxylic acids, including amino acids, di-carboxylic acids, or tartaric acid, including diacyl tartaric acids, in alcohol, preferably ethanol, with stirring at room temperature. The acid salt precipitates from the ethanol solution. The crude isofagomine tartrate acid salt is collected by filtration. The isofagomine solution may be prefiltered to remove any particle impurities before the acid is added. After the addition of the acid, the resulting suspension may be cooled for complete precipitation of the salt.

In another embodiment, the isofagomine acid salt of the present invention may be prepared by adding a substituted carboxylic acid or tartaric acid to a solution wherein isofagomine is prepared in situ without isolation of the isofagomine.

Alternatively, the isofagomine acid salt of the present invention may be prepared from a mineral acid salt of isofagomine such as isofagomine hydrochloride. The conversion can be accomplished by generating isofagomine and subsequently treating the free base with a substitute carboxylic acid. For example, isofagomine free base can be formed by treating with the hydrochloride salt a basic source such as a mineral base, ammonia gas or aqueous ammonium hydroxide solutions, or by exposing it to a solid supported basic resin or a column of basic resin. When a basic resin is used, the resin column can be eluted with water, aqueous ammonium hydroxide or ammonium hydroxide in an alcohol such as methanol, ethanol, IPA, and the like to provide the isofagimine free base, which can be converted to the isofagomine acid salt of the present invention.

Because tartaric acid is a diacid, conversion to the tartaric acid salt can be done with a range of acid to base ratios: 0.5 molar equivalents up to 1 molar equivalent of tartaric relative to isofagomine free base. Tartaric acid can be racemic (the D or -L form) or one of three stereoisomeric forms, the L-(+) form, the D-(−) form, and the meso form. Preferred conditions for making the tartrate salt use ammonium hydroxide solution to generate the free base, 9:1 ethanol/ammonium hydroxide to elute the free base on a silica gel column, evaporation of solvent and excess ammonium hydroxide, formation of the tartrate salt in water/ethanol, and crystallization from water/ethanol.

Isofagomine and tartaric acid can be combined over a range of stoichiometries. Since tartaric acid is a diacid, molar ratios of 2:1 to 1:1 IFG/tartaric acid provide stable salts (see Example 3). The preferred ratio is 1:1. The stoichiometry range is applicable to all isomers of tartaric acid.

The isofagomine scid salt may be purified by using most of commonly used purification methods, preferably recrystallization. For example, crude isofagomine tartrate may be recrystallized in water with and without help of a protic or aprotic co-solvent, preferably alcohol such as, for example, methanol, ethanol, propanols, or butanols. The recrystallization can be effectively conducted not only on small scale but also on industrial scale, e.g., sub-kilogram quantities. Table 1 summarizes purities and yields of several examples prepared and purified accoring to the present invention.

TABLE 1

| Sample No. | Purity (%) | Yield (g) |
|---|---|---|
| 1 | >98 | 5 |
| 2 | >98 | 15 |
| 3 | 96.8 | 55 |
| 4 | 84.5 | 45 |
| 5 | 95.9 | 40 |

TABLE 1-continued

| Sample No. | Purity (%) | Yield (g) |
|---|---|---|
| 6 | 87.4 | 71 |
| 7 | 94.6 | 45 |
| 8 | 95.6 | 343 |
| 9 | 95.8 | 851 |
| 10 | 99.8 | 14 |
| 11 | 98.1 | 134 |
| 12 | 97.6 | 128 |
| 13 | 99.0 | 72 |
| 14 | 99.3 | 116 |
| 15 | 99.5 | 57 |
| 16 | 98.0 | 1368 |

In one preferred embodiment, crude isofagomine tartrate is dissolved in water, and an equal amount of ethanol is added to the resulting solution to get precipitation of the compound. Additional ethanol (1 volume) is then added and stirred. This procedure is repeated for two additional aliquots of ethanol to give an ethanol/water ratio of approximately 4:1. Although most of the isofagomine tartrate will crystallize after adding the first volume of ethanol, additional aliquots can be used for maximization of the yield. After recrystallizing, the solids are filtered and washed. The entire purification can be done at room temperature. Isofagomine tartrate can be purified with this method up to purity about 99% or more. Thus, isofagomine tartrate according to one embodiment of the present invention has purity of 95% or higher, preferably 98% or higher, or even more preferably 99% or higher.

Isofagomine tartrate may also be purified using other solvents or solvent systems such as 1:1 ethanol/water, 1:1 acetone/water, 2:1 ethanol/water, 2:1 acetone/water, or 3:1 ethanol/water. Activated charcoal may also be used to remove any colored impurities. Each of these solvents can provide purities of above 95%, and most have provided purities greater than 98%.

The ease of purification of isofagomine tartrate can be demonstrated by comparing the purification to the purification of the HCl salt of isofagomine in an aqueous solution, which requires lyophilization. Attempts to filter isofagomine-HCl resulted in a substance having a yellow coloration and the consistency of glue. Meanwhile, isofagomine tartrate according to the present invention has good powder characteristics, e.g., crystal size, density, and flowability, that are suitable for a pharmaceutical manufacturing process. Tables 2 and 3 summarize powder characteristics of an isofagomine tartrate sample prepared according to the present invention. Isofagomine tartrate prepared according to present invention is not a fine powder but is mostly populated with middle size particles with bulk density of around 0.44 g/ml and Carr Index of 15%, which thus possess high flowability and easy handling property suitable for a phamaceutical manufacturing process. Isofagomine tartrate obtained according to the above recrystallization process also exhibits consistency in its particle size distribution batch to batch with a baseline span that falls between 0.7 and 1.5, thus avoiding large particles, which may be detrimental to accurate messurement of the salt during the formulation process. Most batches provided more than 98%, or at minimum 90%, of isofagomine tartrate with a particle size of about 1200 μm or less.

TABLE 2

| Sieve Analysis | % Retained |
|---|---|
| 40 | 0.6 |
| 60 | 15.5 |
| 80 | 49.2 |
| 120 | 28.4 |
| 200 | 5.9 |
| 325 | 0.4 |
| >325 | 0.0 |

TABLE 3

| | |
|---|---|
| Bulk Density | 0.44 g/ml |
| Tap Density | 0.52 g/ml |
| Carr Index | 15% |
| Basline span variaton range for 11 batches (average span) | 0.79-1.53 (1.18) |

Furthermore, isofagomine tartrate is not hygroscopic, and the moisture uptake thereof was only about 0.08% after exposure to 75% RH for 8 days. The moisture uptake test results of six different isofagomine tartrate samples prepared according to present invention are ture uptake studies with NaBr saturated solution. summarized in Tables 4 and 5.

TABLE 4

Moisture uptake studies with NaBr saturated solution.

| | 0 hour | 24 hours | 48 hours | 8 days |
|---|---|---|---|---|
| RH | 60% | 59% | 59% | 59% |
| Temperature (° C.) | 19.4 | 20.5 | 20.8 | 20.2 |

| Sample No. | Weight gain (%) | Weight gain (%) | Weight gain (%) | Weight gain (%) |
|---|---|---|---|---|
| 1 | NA | 0.06 | 0.04 | 0.06 |
| 2 | NA | 0.00 | 0.02 | 0.07 |
| 3 | NA | 0.05 | 0.10 | 0.10 |
| Average weight gain (%) | NA | 0.04 | 0.05 | 0.08 |

TABLE 5

Moisture uptake studies with NaCl saturated solution.

| | 0 hour | 24 hours | 48 hours | 8 days |
|---|---|---|---|---|
| RH | 72% | 72% | 71% | 72% |
| Temperature (° C.) | 19.5 | 20.5 | 20.8 | 20.2 |

| Sample No. | Weight gain (%) | Weight gain (%) | Weight gain (%) | Weight gain (%) |
|---|---|---|---|---|
| 1 | NA | 0.02 | 0.05 | 0.10 |
| 2 | NA | 0.00 | 0.00 | 0.00 |
| 3 | NA | 0.08 | 0.8 | 0.15 |
| Average weight gain (%) | NA | 0.04 | 0.05 | 0.08 |

The method for preparing isofagomine tartrate of the present invention is thus suitable to prepare a bulk amount of isofagomine tartrate for pharmaceutical compositions. The bulk amount of isofagomine tartrate prepared according to the invention can be prepared as a slightly crude form that having a purity of about 80% depending upon the purpose of the preparation. However, it also could be prepared as pure as 90% or more, preferably at least 99% with the particle size of about 1200 μm or less for 90% of the isofagomine tartrate.

HPLC may be used to determine both the potency of isofagomine acid salt of the present invention, and the presence of organic impurities. Low wavelength UV detection is suitable for potency calculation versus a reference standard. One of skill in the art may determine proper conditions for the HPLC analysis depending upon the concentration of the sample, the types of the column, solvents, etc. Nonetheless, the following conditions are provided as an example for isofagomine taitrate: the mobile phase may be 10 mM ammonium carbonate ($NH_4HCO_3$)/acetonitrile (CAN) 30/70 in isocratic mode at a flow rate of 0.5 mL/min; the HPLC column may be an Alltech Prevail Carbohydrate column (4.6×150 mm, 5 μm particle size) operated at 50° C.; detection may be set at 210 nm with a 15 minute run time; and samples of drug substance may be dissolved in mobile phase with a 10-μL injection volume.

A charged aerosol detector (CAD) may be used for detection of impurities. Samples may also be analyzed using evaporative light-scattering detection (ELSD) and UV detection. The CAD detector uses evaporative technology to desolvate analytes in the presence of $N_2$ carrier gas. A coronal spark imparts a charge to the $N_2$ gas, which transfers the charge to the analytes. Analytes are detected as they transfer their charger to an electrometer and are measured as current. When the CAD detector is used, the mobile phase may be set to 5 mM ammonium acetate/CAN 50/50 in isocratic mode at a flow rate of 1.0 mL/min with a Primesep 100 (4.6×150 mm, 5 μm particle size) HPLC column operated at 25° C. The samples of drug substance are prepared in mobile phase, and a 10-μL injection volume may be used. The run time for this method is approximately 70 minutes. Impurities are determined using a high/low injection sequence where the sample is quantitated against the reference standard at 1% of the nominal sample concentration.

Identification of isofagomine acid salt of the present invention can be performed using FT-IR and further confirmed by $^1H$ NMR and $^{13}C$ NMR. FIGS. 2-5 show $^1H$, $^{13}C$ NMR, and IR spectra of Isofagomine tartrate prepared according to one embodiment of the present invention. Residual solvents may be monitored by headspace gas chromatohgraphy (GC). Water, residue on ignition, and heavy metals are monitored by standard compendial techniques. Palladium is monitored by ICP spectroscopy as it is the catalyst used in the final hydrogenation step.

Figure 6:
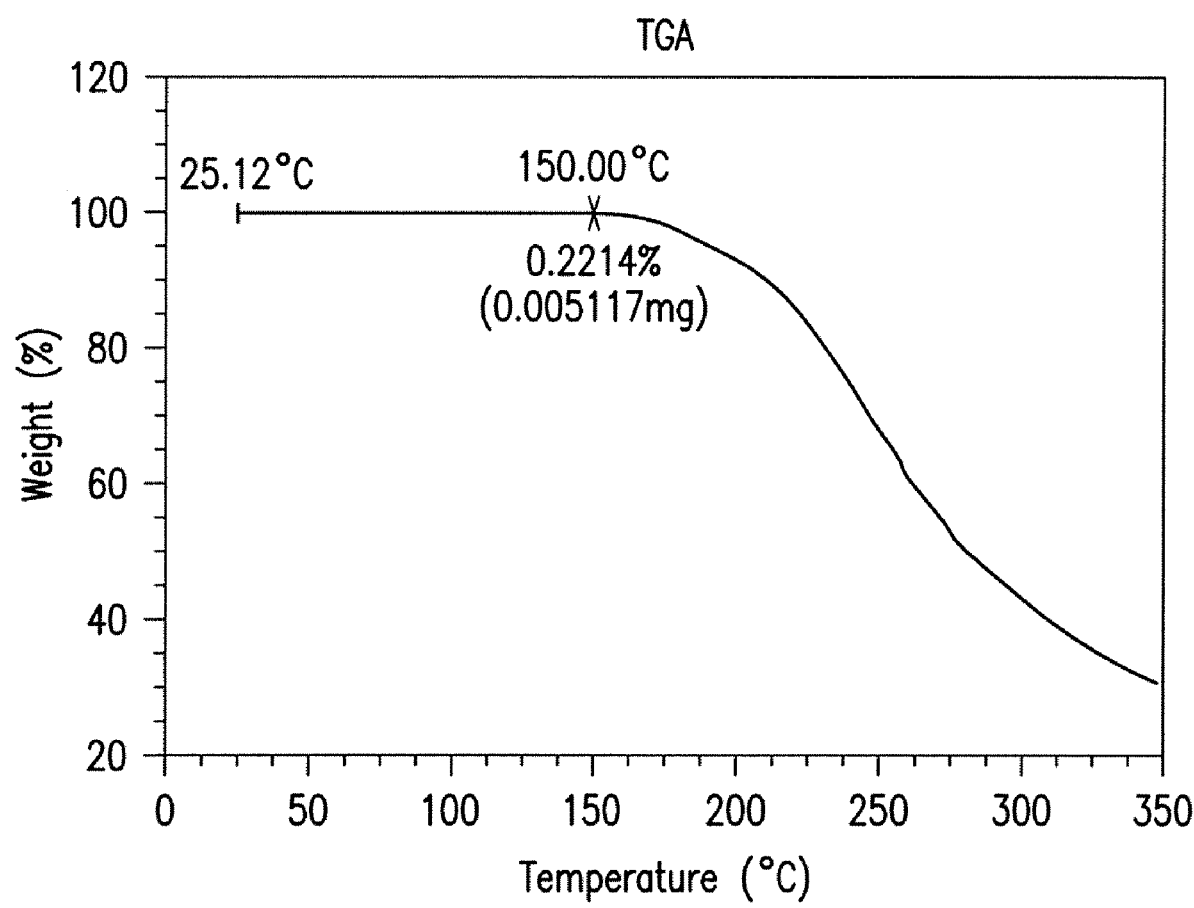
FIG. 6 shows a thermo-gravimetric analysis (TGA) of isofagomine tartrate prepared according to one embodiment of the present invention.
Figure 7:
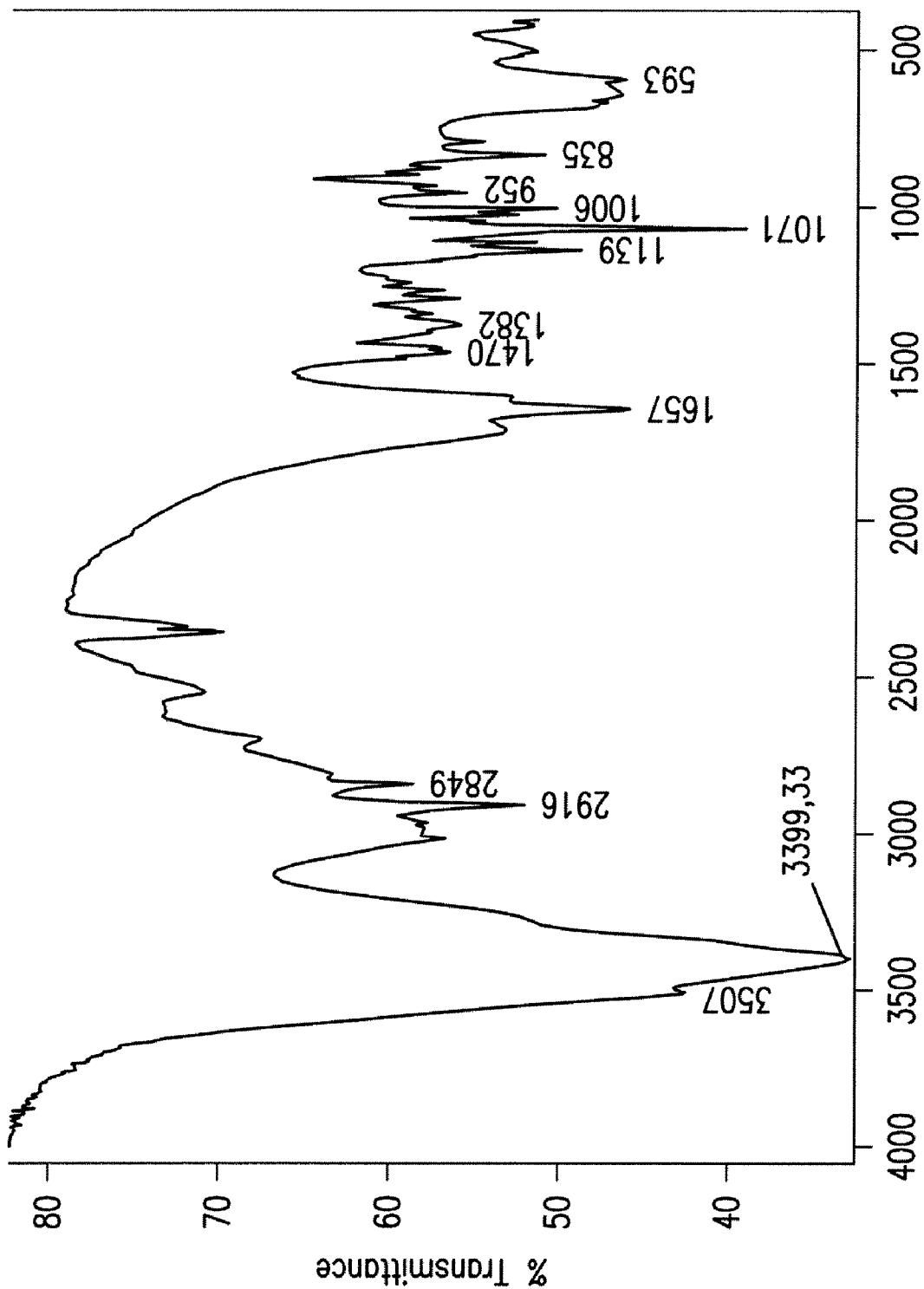
FIG. 7 shows an infrared spectrum of isofagomine tartrate prepared according to one embodiment of the present invention.

FIG. 6 shows an X-ray powder diffraction pattern of isofagomine tartrate prepared according to one embodiment of the present invention. The pattern was obtained using a Bruker D8 Advance diffractometer, and the analysis was performed from 2-45° 2-theta using the following conditions:

| | | | |
|---|---|---|---|
| Divergence slit | 0.6 mm | Anti-scatter slit | 0.6 mm |
| Receiving slit | 0.1 mm | detector slit | 0.6 mm |
| step size | 0.02° | step time | 5 seconds |

Although an X-ray powder diffractogram is useful in identifying a particular solid form of a compound, i.e., polymorphic forms, its 2-theta values as well as intensity and d-spacings may vary because of variations caused during the sample preparation or obtaining the pattern. Also, some margin of error is possible in the assignment of 2-theta and d-spacings. The 2-theta values have a variation of ±0.009. Thus, a preferred method of comparing X-ray powder diffraction patterns in order to identify a particular crystalline form is to overlay the X-ray powder diffraction pattern of the unknown form over the X-ray diffraction pattern of a known form and to compare their characteristic peaks. Nevertheless, the 2-theta, d-spacing, intensity and % intensity values of FIG. 6 are summarized in Table 6. In determining existence of the crystalline form of the present invention in a composition, one may compare five or more most distinctive peaks of those identified in Table 6. The most distinctive peaks include 9.29, 14.17, 16.34, 18.07, 18.72, 19.44, 20.56, 22.13, 23.01, 24.54, and 27.12.

TABLE 6

| Angle (2-Theta °) | d value (Å) | Intensity (Count) | % Intensity (%) |
|---|---|---|---|
| 9.29 | 9.5093 | 131 | 23.3 |
| 14.17 | 6.24684 | 129 | 22.8 |
| 16.34 | 5.42037 | 155 | 27.6 |
| 18.07 | 4.90414 | 330 | 58.5 |
| 18.72 | 4.73704 | 563 | 100 |
| 19.44 | 4.56252 | 165 | 29.3 |
| 20.56 | 4.31573 | 212 | 37.5 |
| 22.13 | 4.01417 | 338 | 60 |
| 23.01 | 3.86164 | 111 | 19.8 |
| 24.54 | 3.62444 | 210 | 37.2 |
| 27.57 | 3.23301 | 276 | 49 |

The Isofagomine acid salt of the present invention can be administered in a form suitable for any route of administration, including, e.g., orally in the form tablets, capsules, or liquid, or in sterile aqueous solution for injection. It can be administered orally in the form of tablets, capsules, ovules, elixirs, solutions or suspensions, gels, syrups, mouth washes, or a dry powder for constitution with water or other suitable vehicle before use, optionally with flavoring and coloring agents for immediate-, delayed-, modified-, sustained-, pulsed-or controlled-release applications. Solid compositions such as tablets, capsules, lozenges, pastilles, pills, boluses, powder, pastes, granules, bullets, or premix preparations may also be used. Solid and liquid compositions for oral use may be prepared according to methods well known in the art. Such compositions may also contain one or more pharmaceutically acceptable carriers and excipients, which may be in solid or liquid form. In a specific embodiment, the isofagomine tartrate is administered as a powder-filled capsule. When the compound is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

The pharmaceutically acceptable excipients also include microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropyl ethylcellulose (HPMC), hydroxypropyl cellulose (HPC), sucrose, gelatin, and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar, or high molecular weight polyethylene glycols. For aqueous suspensions and/or elixirs, the agent may be combined with various emulsifying and/or suspending agents and with diluents such as water, ethanol, propylene glycol and glycerin, and combinations thereof.

Liquid preparations for oral administration may take the form of, for example, solutions, syrups or suspensions, or they may be presented as a dry product for constitution with water or another suitable vehicle (for example, ethanol or a polyol such as glycerol, propylene glycol, and polyethylene glycol, and the like, suitable mixtures thereof, and vegetable oils) before use. Such liquid preparations may be prepared by conventional means with pharmaceutically acceptable additives such as suspending agents (e.g., water, sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). Preparations for oral administration may be suitably formulated to give controlled or sustained release of isofagomine acid salt of the present invention.

The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate, and gelatin.

The pharmaceutical formulations of isofagomine taitrate suitable for parenteral/injectable (for example, by intravenous bolus injection or infusion or via intramuscular, subcutaneous or intrathecal routes) use generally include sterile aqueous solutions, or dispersions and sterile powders for the extemporaneous preparation of sterile injectable solutions or dispersion. The isofagomine tartrate may be presented in unit dose forms, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing, and/or dispersing agents. Alternatively, the active ingredient may be in sterile powder form for reconstitution with a suitable vehicle, e.g., sterile, pyrogen-free water, before use. In all cases, the form must be sterile and must be fluid to the extent that easy syringability exists. It must be stable under the conditions of manufacture and storage and must be preserved against the contaminating action of microorganisms such as bacteria and fungi. The preparation of suitable parenteral formulations under sterile conditions is readily accomplished by standard pharmaceutical techniques well-known to those skilled in the art.

Sterile injectable solutions are prepared by incorporating isofagomine tartrate in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preservatives, stabilizers, dyes, and even flavoring agents may be provided in the pharmaceutical composition. Examples of preservatives include sodium benzoate, ascorbic acid, and esters of p-hydroxybenzoic acid. Antioxidants and suspending agents may be also used.

Additional pharmaceutically acceptable carriers which may be included in the formulation are buffers such as citrate buffer, phosphate buffer, acetate buffer, and bicarbonate buffer, amino acids, urea, alcohols, ascorbic acid, phospholipids, proteins, such as serum albumin, collagen, and gelatin; salts such as EDTA or EGTA, and sodium chloride; liposomes polyvinylpyrolidone; sugars such as dextran, mannitol, sorbitol, and glycerol; propylene glycol and polyethylene glycol (e.g., PEG-4000, PEG-6000); glycerol, glycine or other amino acids and lipids. Buffer systems for use with the formulations include citrate, acetate, bicarbonate, and phosphate buffers. Phosphate buffer is a preferred embodiment.

The formulations can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

The routes for administration (delivery) include, but are not limited to, one or more of: oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

Administration of the above-described parenteral formulations of isofagomine tartrate may be by periodic injections of a bolus of the preparation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014 and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needleless injector devices are described in U.S. Pat. Nos. 5,879,327, 5,520,639, 5,846,233 and 5,704,911, the specifications of which are herein incorporated by reference. Any of the formulations described above can be administered using these methods.

Furthermore, a variety of devices designed for patient convenience, such as refillable injection pens and needle-less injection devices, may be used with the formulations of the present invention as discussed herein.

Typically, a physician will determine the actual dosage which will be most suitable for an individual subject and will provide a therapeutically effective amount to the subject. The specific dose level and frequency of dosage for any particular individual may be varied and will depend upon a variety of factors including the compound activity, the type of Gaucher disease being treated, age, body weight, general health, sex, diet, mode and time of administration, rate of excretion, drug combination, the severity of disease, and the individual undergoing therapy. For oral and parenteral administration, the daily dosage level of the agent may be in single or divided doses. Preferably, the effective amount or dose of the isofagomine acid salt of the present invention is sufficient to increase the level of mutant glucocerebrosidase expression, e.g., to about 3-5%, preferably by about 10%, and more preferably by about 30% of the level found in normal cells, i.e., cells from an individual not having Gaucher disease and/or can ameliorate or prevent a clinically significant deficit GCase activity in the subject.

The effective amount can be often determined by routine experimentation, but is expected to be an amount resulting in serum levels between 0.01 and 100 μM, preferably between 0.01 and 10 μM, most preferably between 0.05 and 2 μM. The effective dose isofagomine tartrate is expected to be between 0.5 and 1000 mg/kg body weight per day, preferably between 0.5 and 100, most preferably between 1 and 50 mg/kg body weight per day. In a specific embodiment, the dose is between about 1-600 mg/day, more specifically 5-300 mg/day, more specifically, 10-150 mg/day. Non-daily dosing also is contemplated. Other dosing regimens contemplated for treatment of Gaucher disease using isofagomine tartrate are described in U.S. provisional patent application 60/914,288, filed on Apr. 24, 2007, which is herein incorporated by reference in its entirety.

The therapeutic monitoring of the present invention is also applicable following treatment of patients with a combination of isofagomine tartrate and another therapy such as ERT or gene therapy. Such combination therapy is described in commonly-owned, U.S. patent application publication numbers 2004/0180419 and 2004/0219132, both of which are herein incorporated by reference in their entirety.

When isofagomine acid salt of the present invention is used in combination with a second therapeutic agent, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician.

When administration is sequential, either the compound of the invention or the second therapeutic agent may be administered first. When administration is simultaneous, the combination may be administered either in the same or different pharmaceutical composition.

When combined in the same formulation, it will be appreciated that the two compounds must be stable and compatible with each other and the other components of the formulation. When formulated separately they may be provided in any convenient formulation, as known for such compounds in the art.

Isofagomine may be synthesized from D-arabinose through an intermediates previously reported in the literature by Danishefski at al. in *Tetrahedron Letters*. 1990; 31(16), 2229. However, the previously reported synthetic steps to the intermediates are not economical for large scale synthesis. The process disclosed herein allows for the reliable and predictable production of those intermediates (and a new intermediate) and the final product on an industrial scal and in high purity. This is because all intermediates are isolated by crystallization, making the process amenable to large scale production.

Isofagomine also may be synthesized the synthesis route shown in Scheme 1.

Scheme 1.

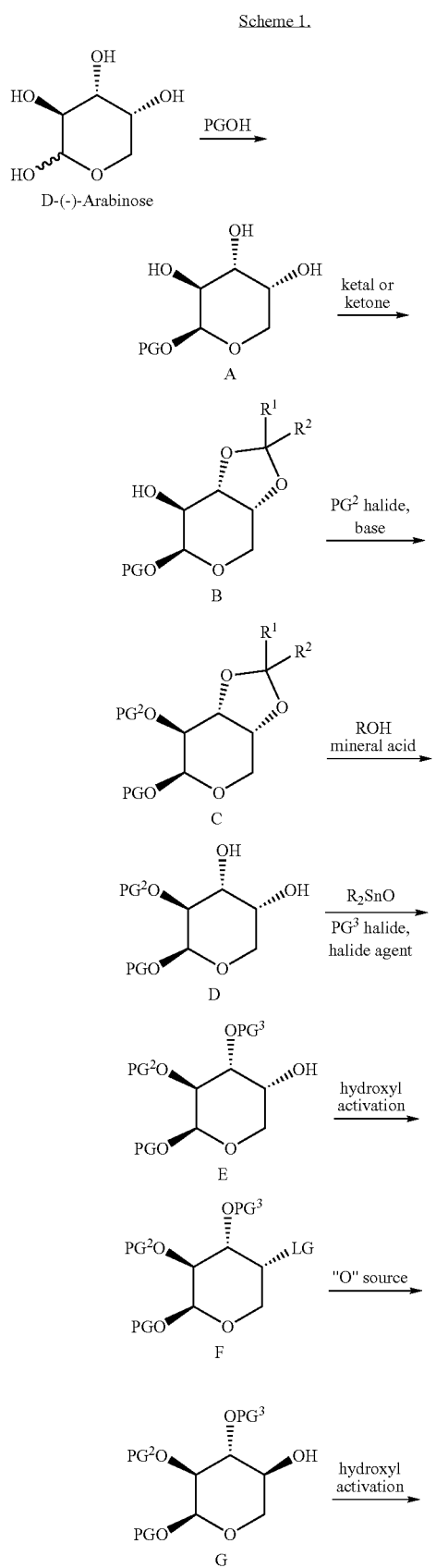

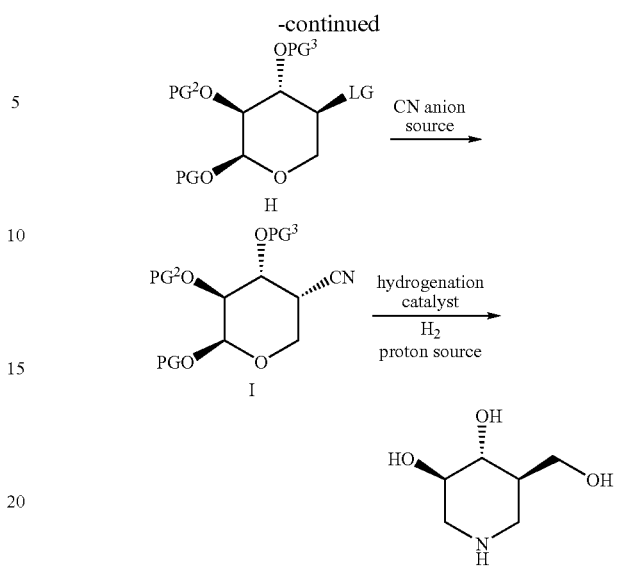

PG is a protecting group; LG is a leaving group

D-Arabinose can be converted to the corresponding protected glycoside (A) using an appropriate alcohol with or without solvent (neat reaction), and an activating agent. For instance the range of alcohols can include benzyl alcohol, or substituted benzyl alcohols such as methoxybenzyl alcohol, chlorobenzyl alcohol, methanol, ethanol, isopropanol, cyclohexylmethyl alcohol and the like in a solvent such as methylene chloride, chloroform, THF, dioxane, DMF, DMA, or NMP, with an activating agent such as HCl, HBr, $H_2SO_4$, or some other mineral acid, or acetyl chloride, propionyl chloride, or another acid chloride of a carboxylic acid. The reaction can be run at temperatures ranging from ambient temperature to about 100° C., for times ranging from 2 to 48 h. For this invention the preferred alcohols are benzyl or substituted benzyl alcohols, and more preferred is benzyl alcohol. Preferred solvents include dioxane, THF or neat reaction, and more preferred is neat reaction. Preferred activating agents include acetyl chloride and $H_2SO_4$, and more preferred is acetyl chloride. Pure product can be readily isolated by precipitation with a non-polar solvent. The preferred solvent and temperature for this product is methyl-t-butyl ether at ambient temperature.

The obtained glycoside of general formula A can be further protected as an acetonide at the 3- and 4-hydroxyl groups by conversion of (A) to ketal (B) with a ketone or a dimethylketal, or enolether thereof, in the presence of an acid, with or without (neat) a polar co-solvent. For instance, aliphatic or aromatic ketones such as acetone, 2-butanone, benzophenone, cyclohexanone, or acetophenone, or their corresponding dialkylketals, can react with a vicinal diol in the presence of an acid such as $H_2SO_4$, p-toluenesulfonic acid, camphorsulfonic acid, or TMS triflate. Co-solvents include methylene chloride, DMSO, DMF, DMA, and NMP. In some cases the ketone can also be the solvent, such as acetone. Reaction temperatures can range from ambient temperature to 100° C. For this reaction, the preferred conditions are acetone and 2,2-dimethoxypropane with p-toluenesulfonic acid at 40° C. Pure product can readily be isolated by crystallization with a two component system including a polar and a non-polar component. Preferred conditions for this purification are ethyl acetate and heptane.

The acetonide (B) can be further protected as an ether at the 2-hydroxyl group by conversion to the corresponding alkoxide followed by subsequent reaction with an alkylating agent to provide a compound of general formula C. Previously reported protection utilized more expensive benzyl bromide and costly silver oxide. Formation of the alkoxide is readily accomplished with a strong base such as and alkali hydride in a polar aprotic solvent such as dialkyl ethers or THF, DMF, DMA, NMP, or DMSO corresponding to PG2. Alkylating agents include benzyl chloride or substituted benzyl. Reaction temperatures can range from −20° C. to 20° C. For this reaction the preferred conditions are sodium hydride in DMF to generate the alkoxide at 0° C. to 10° C., followed by alkylation by benzyl chloride. Pure product can be readily isolated by precipitation with water and a non-polar wash to remove excess water. The preferred non-polar solvent for this purification is heptane.

Removal of the acetonide in the compound of general formula C to provide a diol of general formula (D) is accomplished with a dilute mineral acid such as HCl, HBr, $H_2SO_4$ in an alcohol such as methanol, ethanol, isopropanol, at ambient temperature. For this reaction, the preferred conditions are HCl in methanol at ambient temperature. Pure product (D) can be readily isolated by precipitation with water and a non-polar wash to remove excess water. The preferred non-polar solvent for this purification is heptane.

Additional protection of the diol is required for modification to the target molecule. Selective etherification of the 3-hydroxyl (E) can be accomplished using a tin directed approach in a water-azeotroping solvent at reflux temperatures followed by etherification at moderate temperatures. Tin ethers can be formed using dialkyl or aryl tin(IV) oxides such as diphenyl, dimethyl, dibutyl, diisobutyl, or dioctyltin oxide in aprotic solvents such as benzene, toluene, or xylene. Subsequent alkylation can be accomplished with alkyl or alkylaryl halides such as benzyl bromide or benzyl chloride. The reaction can be accelerated through the use of agents such as CsF or tetraethylammonium chloride, and reaction temperatures can range from ambient temperature to 100° C. For this invention the preferred method uses dibutyltin oxide in toluene and benzyl chloride in the presence of tetrabutylammonium chloride. Purification can be readily accomplished by precipitation of the tin reagent with water. Final product can be obtained by crystallization from a two solvent system. The preferred crystallization solvents for this reaction are ethanol and heptane.

The triprotected intermediate arabinose derivative can be directly converted to the corresponding xylose derivative (G) through an activated system (F). While Mitsunobu inversion is commonly used to invert alcohol configurations, and has been reported for this specific transformation, those conditions are costly on a manufacturing scale. An alternative route involves activation of the arabinose hydroxyl to a discreet, isolable activated system (G) followed by displacement with inversion using an inexpensive oxygen source. Activation can be with esters such as p-toluenesulfonate, methanesulfonate, trifluoromethanesulfonate, an the like, formed from the corresponding anhydride or sulfonyl chloride in the presence of an organic base such as pyridine, collidine, Hunig's base, triethylamine, in a non-polar solvent such as methylene chloride, chloroform, or toluene at temperatures from −20° C. to ambient temperature. Displacement with inversion of the configuration can be accomplished with oxygen nucleophiles, preferably alkali or earth alkali metal nitrite in solvents commonly used for this type of reaction, e.g., methylene chloride, acetone, THF, DMF, DMA, NMP, and the like at temperatures from 0° C. to 40° C. Preferred conditions use trifluoromethanesulfonic anhydride and pyridine in methylene chloride at −10° C. followed by isolation of the triflate without the need for purification. Preferred conditions for displacement of the triflate are sodium or potassium nitrites in DMF at ambient temperature. Purified product can be readily obtained by crystallization from a two solvent system using a polar and a non-polar component. The preferred crystallization solvents for this reaction are isopropanol and heptane.

The triprotected xylose derivative of general formula (H) can be converted into the nitrile (I) with inversion of configuration through an activated system. Similar to the method described above, the route involves activation of the xylose hydroxyl to a discreet, isolable activated system (H) followed by displacement by a cyano source. Activation can be done again with esters of alkyl or aryl sulphonates, preferably p-toluenesulfonate, methanesulfonate, trifluoromethanesulfonate, and the like, which were formed from the corresponding anhydride or sulfonyl chloride in the presence of a mild organic base, such as pyridine, collidine, Hunig's base, triethylamine, and the like in a non-polar solvent such as methylene chloride, chloroform, or toluene at temperatures from −20° C. to ambient temperature. Displacement with inversion of configuration can be accomplished preferably with reagents such as alkali or earth alkali metal cyanides, or tetraethylammonium cyanides in polar, aprotic solvents such as THF, DMF, DMA, NMP, DMSO, and the like at temperatures from 0° C. to 40° C. Preferred conditions use trifluoromethanesulfonic anhydride and pyridine in methylene chloride at −10° C. Preferred conditions for displacement of the triflate are tetraethylammonium cyanide in THF at ambient temperature. Purified product can be obtained by extraction followed by crystallization from an alcoholic solvent. The preferred solvent is ethanol.

Conversion of the nitrile intermediate to isofagomine hydrochloride can be carried out in one step depending on the choice of protecting groups. Nitrile reduction, triple deprotection, ring closure, and hydrogenation of the cyclic imine can be accomplished in a single step under hydrogenation conditions to provide isofagomine in high yield. Catalytic hydrogenation can be carried out with a variety of common catalysts used for such hydrogenation including Pd/C, $Pd(OH)_2$/C, PtO, Degussa catalyst or a combination of catalysts at loadings of 1% to 20%, under hydrogen gas pressure ranging from 14 psi to 100 psi, in protic or aprotic polar solvents, preferably alcohols such as methanol, ethanol, isopropanol, or esters, or acetic acid. The hydrogenation is carried out in the presence of an acid such as HCl, HBr, $HClO_4$, $H_3PO_4$, $H_2SO_4$, acetic acid, triflouroacetic acid, or tartaric acid. The hydrogenation can be run for short or extended periods of time with no risk of product decomposition. Preferred conditions are to run the reaction with a mixture of Pd/C and Pd(OH)2/C with loadings of 5% to 20% under pressures from 40 psi to 100 psi in an alcoholic solvent with HCl. More preferred conditions are 10% loading of Pd/C and 10% loading $Pd(OH)_2$/C under 80 psi hydrogen gas in ethanol with HCl. This hydrochloride salt can be converted to the isofagomine acid salt of the present invention.

Another improved synthesis method for preparation isofagomine and isofagomine tatrate has been recently developed and a separate patent application therefore has been filed. The new method utilizes D-(−)-arabinose or L-(−)-xylose through a diketal intermediate.

To illustrate further the present invention, the following examples are presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification.

COMPARATIVE EXAMPLE A

Purification of Isofagomine Free Base

Isofagomine free base was chromatographed using an Amberlite CG 50 resin column ($NH_4^+$; 2.5 cm ID×100.0 cm L, volume 450 mL). The column was washed with 0.5N $NH_4OH$ solution (3 fold, 1200 mL), then with DI water (5 fold, 2250 mL). Crude isofagomine (1.0 g) was dissolved in 4.0 mL water and loaded onto the column. The column was eluted with 0.1 N $NH_4OH$/water (1.36:1). Fractions of 10 mL were collected.

TLC was performed on the different fractions (silica gel, isopropanol:water:$NH_4OH$ (7:2:1) and detection was via imino sugar and ninhydrin spray. Fractions testing positive with the imino-sugar sprays were analyzed to determine purity, then combined and lyophilized for 72 hours.

COMPARATIVE EXAMPLE B

Purification of Isofagomine-HCl

Isofagomine free base (30 mg) was dissolved in MeOH (5 mL) and 4 N HCl (0.5 mL) in isopropanol and acetone (4.0 mL). The sample was stored refrigerated overnight and filtered. Crystals were observed in the solution. However, when filtered, the product was a yellow substance having a glue-like consistency.

This crude isofagomine-HCl was purified using an ion-exchange chromatography elating with water and ammonia.

Fractions from the ion-exchange column were concentrated by lyophilization to give a gummy semi-solid material.

EXAMPLE 1

Synthesis of IFG Tartrate From D-(−)-Arabinose

Reactions were monitored by TLC and visualized with 5% $H_2SO_4$/methanol, with phosphomolybdic acid solution, or with UV light at 254 nm.

Step 1: D-Arabinose (50 kg, 330.04 moles) and benzyl alcohol (132.2 kg, 4.33 equivalents) were stirred and heated to 35° C. Acetyl chloride (10.9 kg, 0.42 equivalents), keeping the temperature <45° C., then stirred 50° C. overnight. The mixture was cooled to 20° C. and diluted with MTBE (600 kg). The mixture was stirred for 0.5-5 h. The solids were collected by filtration and washed with MTBE (2×40 kg). The material was dried in a filter drier. 2-Benzyl-D-arabinose was obtained as an off-white solid, 70.9 kg (88.6%). $^1$H NMR (300 MHz, DMSO-$d_6$): δ 7.32 (m, 5H), 4.76 (s, 1H), 4.66 (d, J=12 Hz, 1H), 4.59 (m, 3H), 4.45 (d, J =12 Hz, 1H), 3.70 (m, 4H), 3.47(dd, J=12, 3 Hz, 1H).

Step 2: 2-Benzyl-D-arabinose (73.5 kg, 305.92 moles) was mixed with acetone (522 kg). 2,2-Dimethoxypropane (26.6 kg, 1.9 equivalents) was added in one portion followed by p-toluenesulfonic acid monohydrate (39.3 g, 0.0007 equivalents). The mixture was stirred at 40° C. for 18 hours. After the reaction was complete, triethylamine (193 mL, 0.0046 equivalents) was added. The solvents were removed at 30° C. under reduced pressure until a thick oil was obtained. The residue was co-evaporated with ethyl acetate (2×20 kg). Ethyl acetate (19.2 kg) was added to form a solution. Heptane (145.8 kg) was added in one portion to the solution and cooled to −10° C. to 0° C. over night. The solids were collected by filtration and washed with heptane (2×51.5 kg). The material was dried in a filter dryer with a nitrogen purge. The acetonide derivative (3aR,6R,7S,7aS)-6-(beiizyloxy)-2,2-dimethyltetrahydro-3H-[1,3]dioxolo[4,5-c]pyran-7-ol was obtained as an off-white solid, 70.4 kg (82%). m.p. 58-59 ° C. $^1$H NMR (400 MHz, CDCl$_3$): δ 7.34 (m, 5H), 4.92 (d, J=4 Hz, 1H), 4.79 (d, J=12 Hz, 1H), 4.54 (d, J=12 Hz, 1H), 4.20 (m, 2H), 4.00 (dd, J=13, 3 Hz, 1H), 3.92 (dd, J =13, 2 Hz, 1H), 3.80 (m, 1H), 2.24 (d, J=7Hz, 1H), 1.52 (s, 3H), 1.35 (s, 3H).

Step 3: The acetonide derivative (78.2 kg, 278.97 moles) was mixed with DMF (295 kg, 3.77 kg/kg starting material) and cooled to 5° C. Sodium hydride (13.4 kg, 1.2 equivalents) was added to the reactor in 3 to 4 portions, maintaining the reaction mixture below 10° C. then stirred for 1.5 hours. At a temperature of 2° C., benzyl chloride (45.9 kg, 1.3 equivalents) was added over a 1 hour period. The reaction was stirred at 10° C. to 15° C. for 12 h. After the reaction was complete, the mixture was cooled to 2° C. and water (20 kg) was added over 1 h. An additional charge of water (570 kg) was added over 4 hours. The mixture was stirred at this temperature for 10 h. The product was collected by centrifuge filtration and washed with water (2×10 kg) and heptane (2×15 kg) spun dry overnight. The dibenzyl derivative (3aR,6R,7S,7aR)-6,7-bis (benzyloxy)-2,2-dimethyltetrahydro-3aH-[1,3]dioxolo[4,5-c]pyran was obtained as a white solid, 74.0 kg (71.6%).

Step 4: The dibenzyl derivative (37.6 kg, 101.50 moles) was added to methanol, AR (259 kg, 8.7 kg/kg starting material) and the contents were cooled to 15° C. A 2.5 N HCl solution (76.2 kg, 1.8 equivalents) was added over 1 hour. Additional water (20 kg) was added and the mixture was stirred for 12 hours at 15° C. Water (1035 kg, 4×vol methanol, AR) was added to the reactor and stirred for at least 0.5 h. The product was filtered onto a centrifuge and washed with water (2×10 kg) and heptane (2×15 kg) and spun dry overnight. The diol (3R,4R,5S, 6R)-5,6-bis(benzyloxy)tetrahydro-2H-pyran-3,4-diol was obtained as a white solid, 31.5 kg (94%).

Step 5: The diol derivative (37.5 kg, 113.51 moles) was mixed with toluene (207.6 kg, 5.5 kg/kg of diol) and dibutyltinoxide (31.1 kg, 1.1 equivalents). The reactor was equipped with a Dean-Stark apparatus and the reactor contents were heated to reflux (approx. 110° C.) until water no longer collected for removal (8-12 h). The reactor contents were cooled to 35° C. and tetrabutylammonium chloride (18.3 kg, 0.5 equivalents) was added in one portion. Benzyl chloride (15.8 kg, 1.1 equivalents) was added at a rate that kept the temperature <40° C. and stirring continued at 35° C. for 12 h. The addition and 12 h stirring were repeated daily for 4 days until the reaction was complete. After the reaction was complete, the mixture was cooled to 25° C., water (150 kg) was added in one portion, and the contents were stirred overnight. The reaction mixture was filtered through a bed of Celite (1 kg/kg of diol) and the bed was rinsed with toluene (10 kg). The filtrate was allowed to settle (1 h) and the layers were separated. Water addition, stirring, filtration, and separation were repeated. The aqueous layers were combined and extracted with ethyl acetate (25 kg), and the layers were separated. The organic layers were combined and concentrated under vacuum at 45° C. to a minimum stirable volume. Heptane (102.6 kg) was added. The mixture was stirred for 20 minutes, cooled to 0° C., and stirred for 8-12 h. The solids were collected by filtration and washed with heptane (10 kg). Crude solids were dissolved in 6:1 heptane/200 pf ethanol (7 kg/kg crude solid) at 35° C., cooled to −5° C. to 0° C. and stirred overnight. The solids were collected by filtration and washed with heptane (10 kg). The product purity was monitored by TLC. Typically, 2 or more re-crystallizations were required to remove the impurities. The purified tribenzyl derivative was dried in a vacuum oven at 30° C. (3R,4R,5S, 6R)-4,5,6-Tris(benzyloxy)tetrahydro-2H-pyran-3-ol was obtained as a white solid, 17.5 kg (37%). m.p. 59-60° C. $^1$H NMR (400 MHz, CDCl$_3$): δ 7.38 (m, 15H), 4.89 (d, J =4 Hz, 1H), 4.82 (d, J=12 Hz, 1H), 4.71 (m, 3H), 4.57 (d, J=12 Hz, 1H), 4.55 (d, J=12 Hz, 1H), 4.01 (br s, 1H), 3.95 (dd, J=10, 3 Hz, 1H), 3.83 (m, 2H), 3.71 (dd, J=12, 2 Hz, 1H), 2.56 (br s, 1H).

Step 6: The tribenzylarabinose derivative (12.0 kg, 28.54 moles) was mixed with methylene chloride (79.2 kg, 6.6 kg/kg starting material) and pyridine (11.3 kg, 5 equivalents) and cooled to −10° C. Trifluoromethanesulfonic anhydride (10.1 kg, 1.25 equivalents) was added at a rate that kept the temperature below 0° C. The reaction mixture was stirred at −10° C. to 0° C. until starting material was consumed. Once complete, the reaction mixture was washed with 7.5% HCl solution (3×68 kg, 17 equivalents) and water (48 kg). During the washes, the temperature of the reaction mixture was maintained at <5° C. The mixture was adjusted to pH≧6 by washing with 7.5% NaHCO$_3$ solution (55.0 kg). Triethylamine (0.4 kg, 0.3 kg/kg starting material) was added and the organic phase was dried with anhydrous K$_2$CO$_3$ (1.2 kg, 0.1 equivalents). The mixture was filtered and concentrated to dryness under vacuum at 20° C. to 35° C. to give (3S,4R,5S, 6R)-4,5,6-Tris(benzyloxy)tetrahydro-2H-pyran-3-ol. The triflate was used without purification. $^1$H NMR (300 MHz, CDCl$_3$): δ 7.31-7.16 (m, 15H), 5.12 (br s, 1H), 4.83 (d, J=4 Hz, 1H), 4.76 (d, J=11 Hz, 1H), 4.64 (m, 2H), 4.50 (d, J=9 Hz, 1H), 4.46 (d, J=8 Hz, 1H), 3.97 (dd, J=10, 3 Hz, 1H), 3.86 (d, J=14 Hz, 1H), 3.77-3.72 (m, 2H).

Step 7: The triflate was dissolved in DMF (36.2 kg, 3.02 kg/kg starting material) and cooled to 10° C. Sodium nitrite (5.9 kg, 3.0 equivalents) was added, the solution exothermed to approximately 30° C., then the reaction mixture was cooled to 15° C. to 25° C. and stirred for 12-16 h. The mixture was cooled to 5° C., and water (152 kg, 4.2 kg/kg DMF) was added at a rate that kept the temperature <15° C. The resulting mixture was agitated at 10° C. for 2 hours. The solids were filtered and washed with water (2×12 kg). The filtered solids were dissolved in ethyl acetate (21.6 kg, 1.8 kg/kg starting material). The solution was washed with brine (15.5 kg), dried with MgSO$_4$ (2.5 kg), filtered, and the filtrate was concentrated to dryness under vacuum at 35° C. Isopropanol (9.5 kg) was added and heated to 75° C. to dissolve the crude product. Heptane (24.6 kg) was added to the solution and the mixture cooled to 15° C. to 25° C. The mixture was further cooled to 0° C. and stirred overnight. The solids were filtered and washed with heptane (2×8.2 kg). The material was dried in a vacuum oven. (3S,4R,5S,6R) -4,5,6-Tris(benzyloxy)tetrahydro-2H-pyran-3-ol was obtained as a yellow solid, 5.3 kg (44%). $^1$H NMR (300 MHz, CDCl$_3$): δ 7.37 (m, 15H), 4.96 (d, J=11 Hz, 1H), 4.80 (m, 2H), 4.68 (d, J=12 Hz, 1H), 4.61 (m, 2H), 4.53 (d, J=12 Hz, 1H), 3.78 (m, 1H), 3.67 (m, 3H), 3.50 (dd, J=9, 3 Hz, 1H), 2.42 (br s, 1H).

Step 8: The tribenzylxylose derivative (10.4 kg, 24.73 moles) was mixed with methylene chloride (68.6 kg, 6.6 kg/kg starting material) and pyridine (9.8 kg, 5 equivalents) and cooled to −10° C. Trifluoromethanesulfonic anhydride (8.7 kg, 1.25 equivalents) was added at a rate that kept the temperature below 0° C. The reaction mixture was stirred at −10° C. to 0° C. until starting material was consumed. Once complete, the reaction mixture was washed with 7.5% HCl solution (3×58.9 kg, 17 equivalents) and water (41.6 kg). During the washes, the temperature of the reaction mixture was maintained at <5° C. The mixture was adjusted to pH≧6 by washing with saturated NaHCO$_3$ solution (44.6 kg). Triethylamine (0.4 kg, 0.3 kg/kg starting material) was added and the organic phase was dried with anhydrous K$_2$CO$_3$ (1.2 kg, 0.1 equivalents). The mixture was filtered and concentrated to dryness under vacuum at 20° C. to 35° C. NMR?

Step 9: The triflate was dissolved in THF (29 kg, 2.8 kg/kg starting material) and cooled to 10° C. Tetraethylammonium cyanide (4.6 kg, 1.2 equivalents) was added, the solution exothermed, then the reaction mixture was cooled to 20° C. and stirred for 12 h. Ethyl acetate (21.8 kg) was added and the organic phase was washed with 10% NaCl solution (3×14.3 kg). The combined aqueous layers were extracted with ethyl acetate (21.8 kg). The organic layers were combined, dried with MgSO$_4$ (2 kg), filtered, and concentrated to dryness under. Ethanol (200 pf, 3.23 kg/kg starting material) was added and heated to 70° C. to dissolve the crude product. The solution was cooled to 20° C., then further cooled to 5° C. and stirred overnight. The solids were filtered and washed with heptane (2×10.4 kg). Crystallization from 200 pf ethanol (7 mL/g solids) was repeated. The solids were filtered and washed with heptane (2×10.4 kg). The material was dried in a vacuum oven. (3R,4R,5S,6S)-4,5,6-Tris(benzyloxy)tetrahydro-2H-pyran-3-carbonitrile was obtained as a light brown solid, 6.3 kg (59%). $^1$H NMR (300 MHz, CDCl$_3$): δ 7.31 (m, 15H), 4.90 (d, J=3 Hz, 1H), 4.81-4.73 (complex, 3H), 4.70 (d, J=12 Hz, 1H), 4.62 (d, J=12 Hz, 1H), 4.55 (d, J=12 Hz, 1H), 3.99 (dd, J=9, 5 Hz, 1H), 3.91 (dd, J=12, 3 Hz, 1H), 3.82-3.74 (overlapping signals, 2H), 3.13 m, 1H).

Step 10: The nitrile derivative (2.5 kg, 5.8 moles) was dissolved in absolute ethanol (138.1 kg) and heated at 35° C. until a clear solution was obtained. Moistened palladium on carbon was added (250 g; 10% w/w), followed by palladium hydroxide, (250 g; 20% w/w) and hydrochloric acid (0.6 L). The solution was purged twice with nitrogen and once with hydrogen. The solution was pressurized to 80 psi with hydrogen, stirred, and heated to 35° C. for 72 hours, repressurizing as necessary. The mixture was filtered and concentrated under vacuum at 30° C. to 35° C. Crude isofagomine hydrochloride was mixed with aq NH$_4$oH (3 L). The solution was filtered and purified on a silica gel column (approx 20 kg) using 9:1 EtOH/aq NH$_4$OH solvent system. The product was concentrated under vacuum at 35° C. to 40° C. The isofagomine free base was dissolved in absolute ethanol (7.7 mL/g residue) and filtered. L-(+)-Tartaric acid (1185 g, 1 g/g residue) was dissolved in absolute ethanol (7.7 mL/g residue), filtered, and slowly added to the solution of isofagomine in ethanol. This solution was stirred for 45 minutes, filtered, and washed with ethanol (2.5 L, 1 mL/g starting material). The product was dried to constant weight in a vacuum oven at 44° C. Isofagomine tartrate was obtained as a white solid 1.2 kg (97.5% purity). 1H NMR (300 MHz, D20): δ 4.40 (s, 2H), 3.70 (dd, J=12, 4 Hz, 1 H), 3.66-3.58 (m, 2H), 3.38 (m, 3H), 2.83 (t, J=13 Hz, 1H), 2,79 (t, J=13 Hz, 1H), 1.88-1.77 (m, 1H).

EXAMPLE 2

Recrystallization of Isofagomine Tartrate

Figure 3:
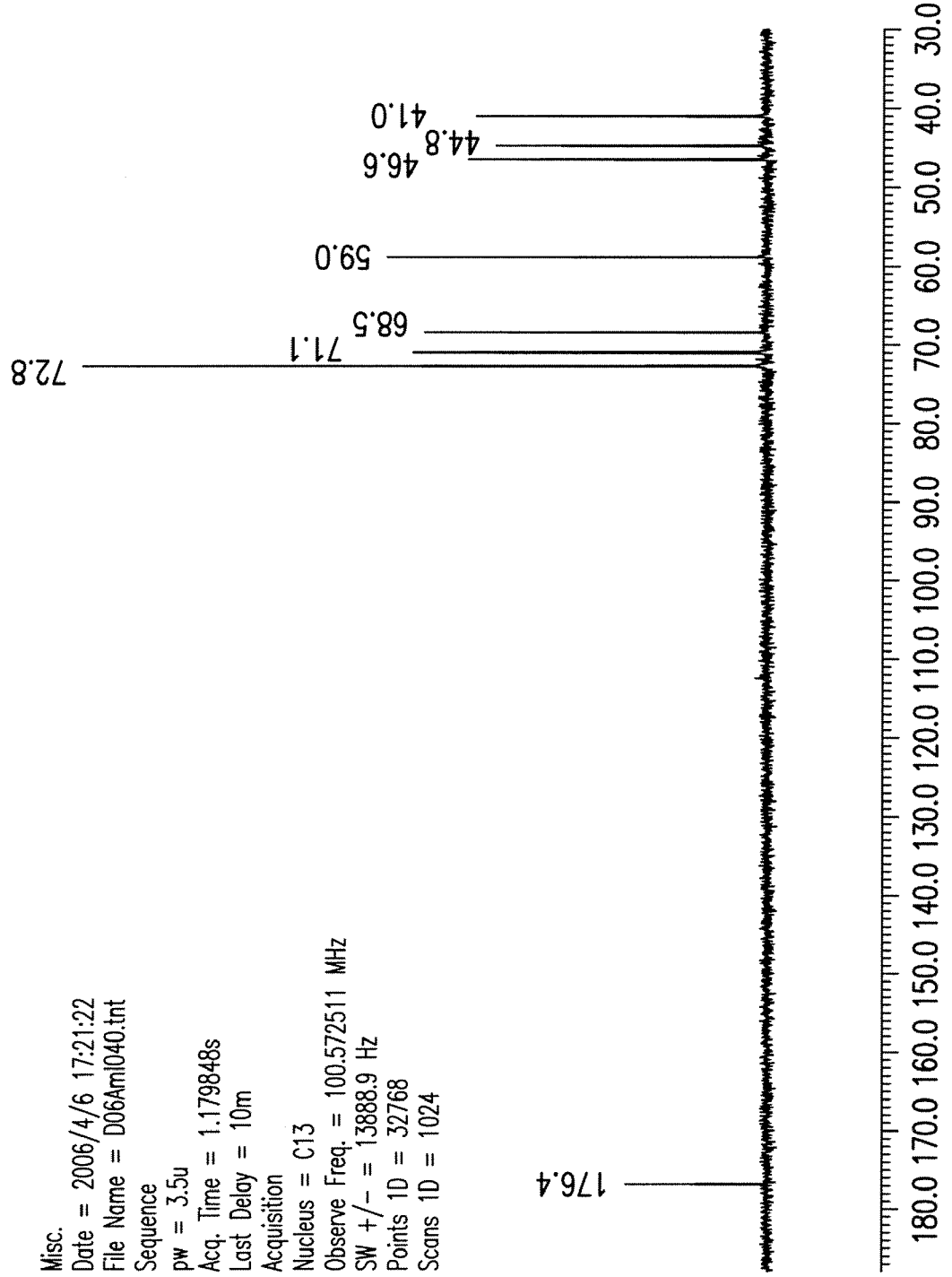
FIG. 3 show a $^{13}$C NMR in $D_2O$ of isofagomine tartrate prepared according to one embodiment of the present invention.
Figure 4:
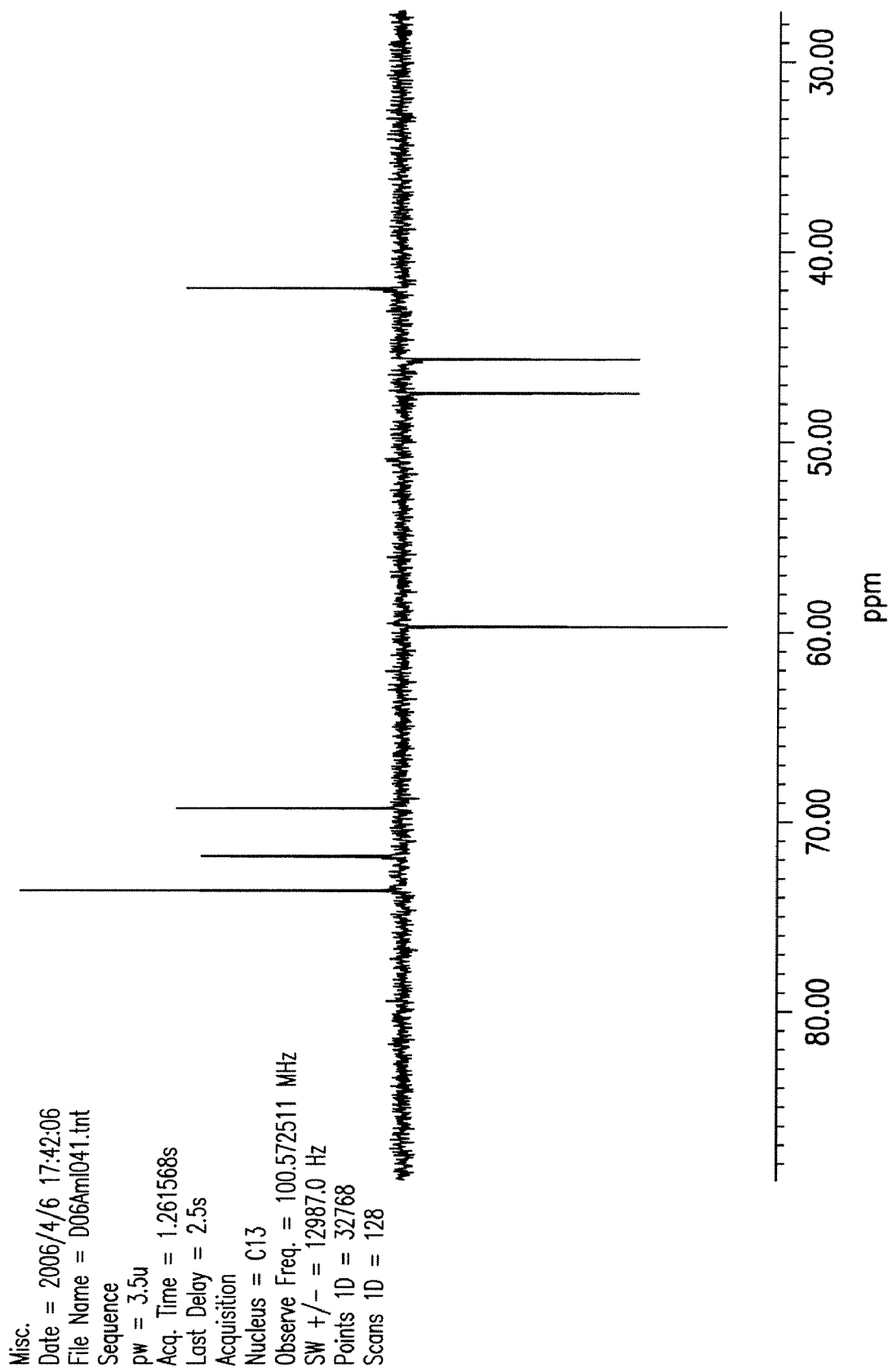
FIG. 4 shows a spin-echo $^{13}$C NMR in $D_2O$ of isofagomine tartrate prepared according to one embodiment of the present invention.
Figure 5:
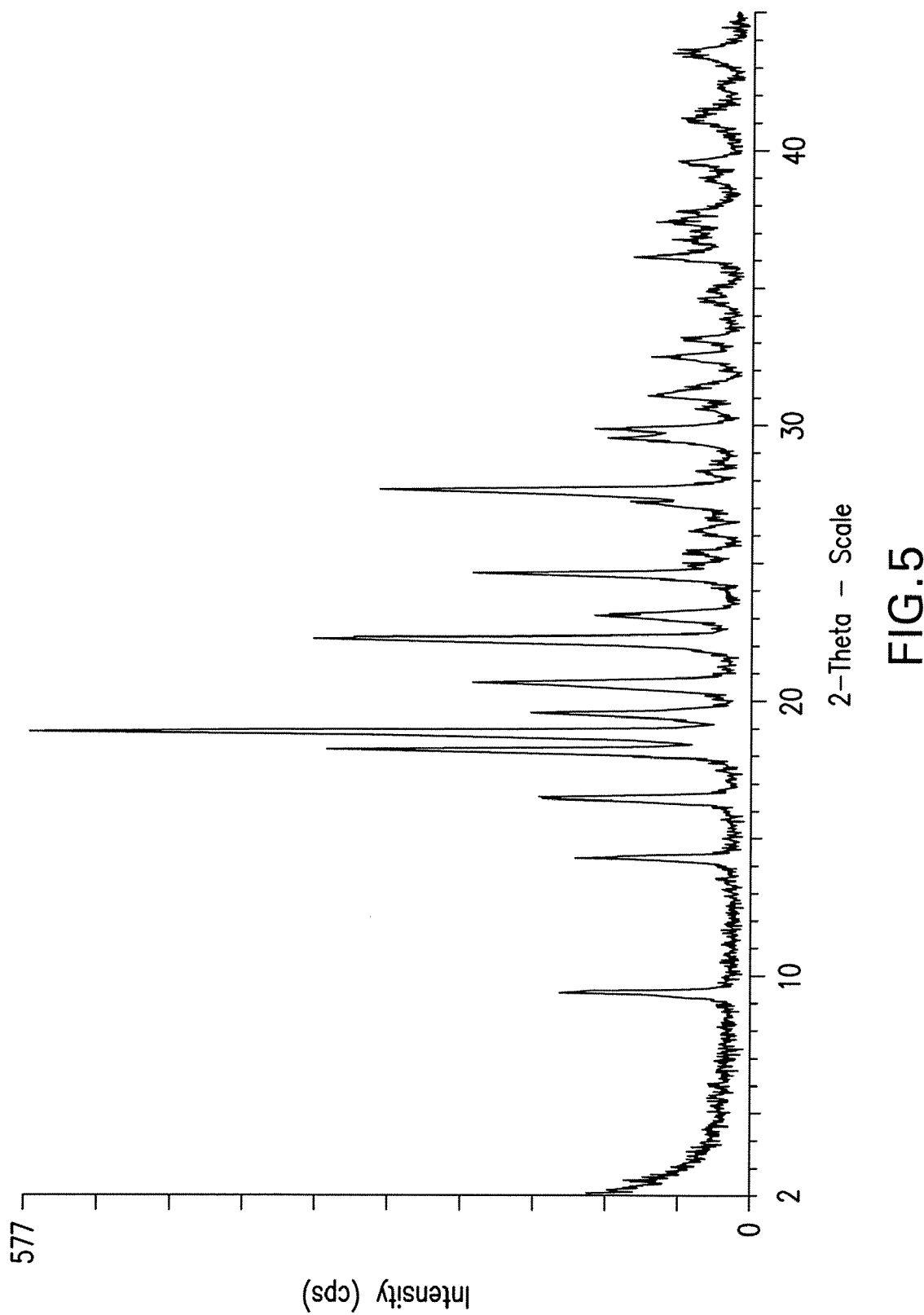
FIG. 5 shows an X-ray powder diffraction pattern of isofagomine tartrate prepared according to one embodiment of the present invention.

Isofagomine tartrate (1,767 g) was dissolved in water (1.767 L) at ambient temperature. Absolute EtOH (1.767 L) was added and stirred for over 30 minutes. An additional aliquot of absolute EtOH (1.767 L) was added dropwise at a slow stream and stirred for 30 minutes. This process was repeated twice (including the 30-minute of stirring) to obtain a solution of 4:1 EtOH/water. The solids were filtered and washed with EtOH/water (4:1) and dried in a vacuum oven at 43° C. overnight to a constant weight (i.e., <1% net weight loss after re-drying for an additional 2 hours). The yield from recrystallization was 91%. The sample was found to have 1.3% impurities based on HPLC. NMR spectra of the recrystallized product are shown in FIG. 3 and FIG. 4. m.p. 168-169° C.

EXAMPLE 3

Synthesis of Isofagomine Tartrate Salts

Isofagomine L(+)-Tartrate salt (2:1)

Figure 8A:
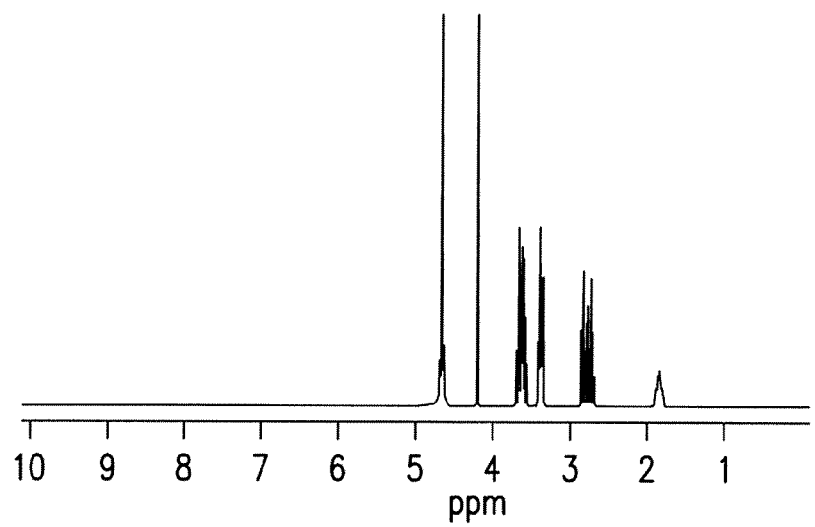
FIG. 8A shows an $^1$H NMR ($D_2O$) of Isofagomine L-(+)-Tartrate salt (2:1) prepared according to one embodiment of the present invention.

A solution of L-(+)-tartaric acid (102 mg, 0.679 mmol) in deionized water (1.0 mL) was added into the solution of isofagomine (200 mg, 2.0 equivalents) dissolved in deionized water (2.0 mL) at room temperature. The solution was stirred for 10 min and lyophilized overnight. The residue was further dried under vacuum at 45° C. for three days to afford the desired salt (275.6 mg, 91%). m.p. 92-93° C., $^1$H NMR (300 MHz, D$_2$O): δ 4.22 (s, 2H), 3.71 (dd, J=12, 3.6 Hz, 1H), 3.67-3.59 (m, 2H), 3.44-3.37 (m, 3H), 2.85 (t, J=12 Hz, 1H), 2.75 (t, J=12 Hz, 1 H), 1.85 (m, 1H) (FIG. 8A)

Isofagomine D-(−)-Tartrate Salt (2:1)

Figure 8B:
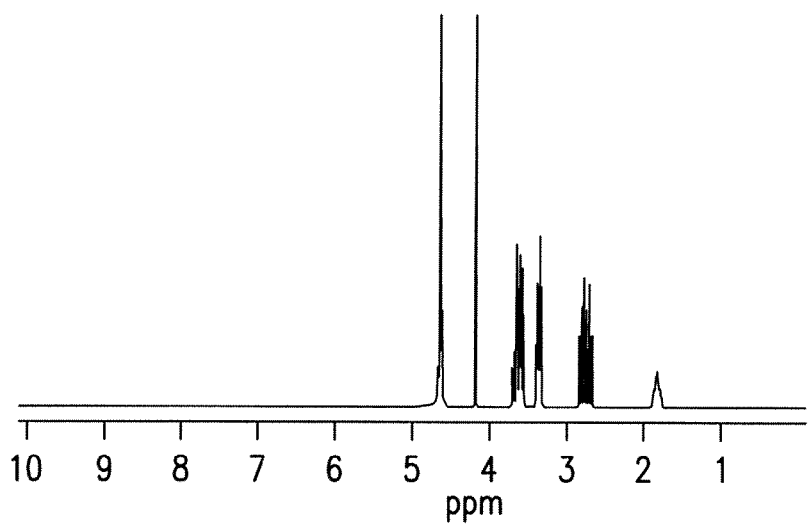
FIG. 8B shows an $^1$H NMR ($D_2O$) of Isofagomine D-(−)-Tartrate salt (2:1) prepared according to one embodiment of the present invention.

A solution of D-(-)-tartaric acid (102 mg, 0.679 mmol) in deionized water (1.0 mL) was added into the solution of isofagomine (200 mg, 2.0 equivalents) dissolved in deionized water (2.0 mL) at room temperature. The solution was stirred for 10 min and lyophilized overnight. The residue was further dried under vacuum at 45° C. for three days to afford the desired salt (287.2 mg, 95%). m.p. 94-95° C., $^1$H NMR (300 MHz, D$_2$O): δ 4.22 (s, 2H), 3.71 (dd, J=12, 3.6 Hz, 1H), 3.67-3.59 (m, 2H), 3.44-3.36 (m, 3H), 2.85 (t, J=12 Hz, 1H), 2.75 (t, J=12 Hz, 1 H), 1.84 (m, 1H) (FIG. 8B).

Isofagomine D-(−)-Tartrate Salt (1:1)

Figure 8C:
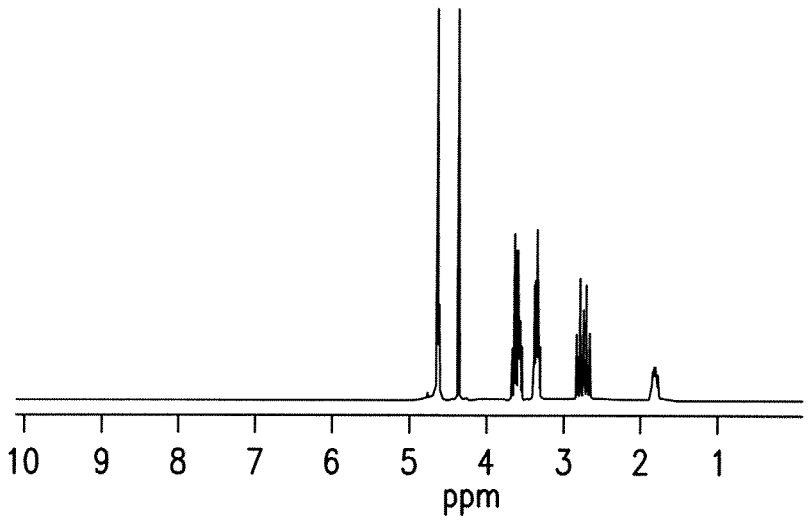
FIG. 8C shows an $^1$H NMR ($D_2O$) of Isofagomine D-(−)-Tartrate salt (1:1) prepared according to one embodiment of the present invention.

A solution of D-(-)-tartaric acid (204 mg, 1.359 mmol) in deionized water (2.0 mL) was added into the solution of isofagomine (200 mg, 2.0 equivalents) dissolved in deionized water (2.0 mL) at room temperature. The solution was stirred for 10 min and lyophilized overnight. The residue was further dried under vacuum at 45° C. for three days to afford the desired salt (396.9 mg, 98%). m.p. 73-74° C., $^1$H NMR (300 MHz, D$_2$O): 6 4.41 (s, 2H), 3.71 (dd, J=12, 3.3 Hz, 1H), 3.66-3.59 (m, 2H), 3.44-3.36 (m, 3H), 2.84 (t, J=12 Hz, 1H), 2.75 (t, J=12 Hz, 1 H), 1.84 (m, 1H) (FIG. 8C)

EXAMPLE 4

Formulations of Isofagomine Tartrate Capsule

|  | 10 mg Capsule, Prototype 1 | | | 100 mg Capsule, Prototype 2 | | |
| --- | --- | --- | --- | --- | --- | --- |
|  | % w/w | mg/capsule | g/batch | % w/w | mg/capsule | g/batch |
| Isofagomine tartrate | 5.50 | 10.00 | 15.00 | 50.00 | 100.00 | 40.00 |
| Avicel PH102 ® (microcrystalline cellulose) | 94.00 | 170.79 | 256.19 | 49.50 | 99.00 | 39.60 |
| Magnesium Stearate | .050 | .091 | 1.36 | 0.50 | 1.00 | .040 |
| Total | 100.00 | 181.70 | 272.55 | 100.00 | 200.00 | 80.00 |
| opaque white capsule shells, size tbd | | 1500 capsules (estimated shell size = 2 or 3) | | | 400 capsules (estimated shell size = 2 or 3) | |
|  | 10 mg Capsule, Prototype 3 | | | 100 mg Capsule, Prototype 4 | | |
|  | % w/w | mg/capsule | g/batch | % w/w | mg/capsule | g/batch |
| Isofagomine tartrate | 4.35 | 10.00 | 15.00 | 40.00 | 100.00 | 40.00 |
| Emcompress ® (dibasic calcium phosphate) | 47.43 | 109.08 | 163.62 | 29.60 | 74.00 | 29.60 |
| Avicel PH102 ® (microcrystalline cellulose) | 47.43 | 109.08 | 163.62 | 29.60 | 74.00 | 29.60 |
| Cab-O-Sil ® (colloidal (fumed) silicon dioxide) | .30 | .69 | 1.04 | .30 | .75 | .30 |
| Magnesium Stearate | 0.50 | 1.15 | 1.73 | .050 | 1.25 | .050 |
| Total | 100.00 | 230.00 | 345.00 | 100.00 | 250.00 | 100.00 |
| opaque white capsule shells, size tbd | | 1500 capsules (estimated shell size = 2 or 3) | | | 400 capsules (estimated shell size = 2 or 3) | |

EXAMPLE 5

Intracellular Enhancement of GCase Activity in Fibroblasts from Gaucher Patients The Intracellular Enhancement activity of isofagomine L-(+)-tartrate was investigated with fibroblasts established from Gaucher patients. To evaluate the effects of IFG on mutant GCase levels, an ex vivo response study with macrophages and EBV-transformed lymphoblasts derived from peripheral leukocytes of 40 patients was conducted.

The study included 21 males with type I Gaucher disease, 1 male with type III Gaucher disease, and 18 females with type I Gaucher disease. Patients ranged in age from 7 to 83 years, and 38 of 40 patients were on enzyme replacement therapy (ERT). Macrophages were successfully derived from 34 of 40 patients, of which 32 demonstrated a dose-dependent increase in GCase levels (average=2.8-fold) when treated with IFG tartrate (5 days). Similar results were observed for 5 additional patient-derived lymphoblast cell lines. IFG significantly increased GCase levels in cells from patients with different genotypes including N370S/N370S (11), N370S/L444P (8), N370S/84insG (11), N370S/R163X, N370S/Y212H, L444P/del 136T, L444P/F216Y, L444P/L174F, G202R/R463C, and K79N/complex B exon 9/10 (type III GD). Maximum enhancement of GCase in macrophages was achieved at about 30 μM of IFG.

EXAMPLE 6

Phase I Studies of the Safety, Pharmacokinetics and Pharmacodynamics of Isofagomine Tartrate, a New Pharmacological Chaperone for the Treatment of Gaucher Disease Isofagomine tartrate is a pharmacological chaperone in development for the treatment of the lysosomal storage disorder Gaucher disease. Using cell-based and animal models we have shown that isofagomine increases cellular levels of glucocerebrosidase (GCase), the enzyme deficient in Gaucher disease. Randomized double-blind Phase I clinical studies were performed in 72 healthy volunteers, (39 male, 33 female). Isofagomine tartrate was orally administered as an aqueous solution. In a first-in-human single ascending dose study, doses of 8, 25, 75, 150 (two cohorts), and 300 mg were administered (6 active, 2 placebo in each cohort). In a multiple ascending dose study, doses of 25, 75, and 225 mg were administered daily for seven days (6 active, 2 placebo in each cohort). In both studies, isofagomine tartrate was generally well tolerated at all doses and treatment-emergent adverse events in both studies were mostly mild. No serious adverse events occurred.

Isofagomine tartrate showed good systemic exposure via the oral route. In the single-dose study, plasma AUC and Cmax values were linearly correlated with administered dose. Mean plasma levels peaked at 3.4 hr. (SEM: 0.6 hr.) and the plasma elimination half-life was 14 hr. (SEM: 2 hr.). In the multiple-dose study, after 7 days of oral administration, the pharmacokinetic behavior was found to be linear with dose, with no unexpected accumulation of isofagomine. Tmax and half-life values were similar to those observed in the single-dose study.

Figure 9:
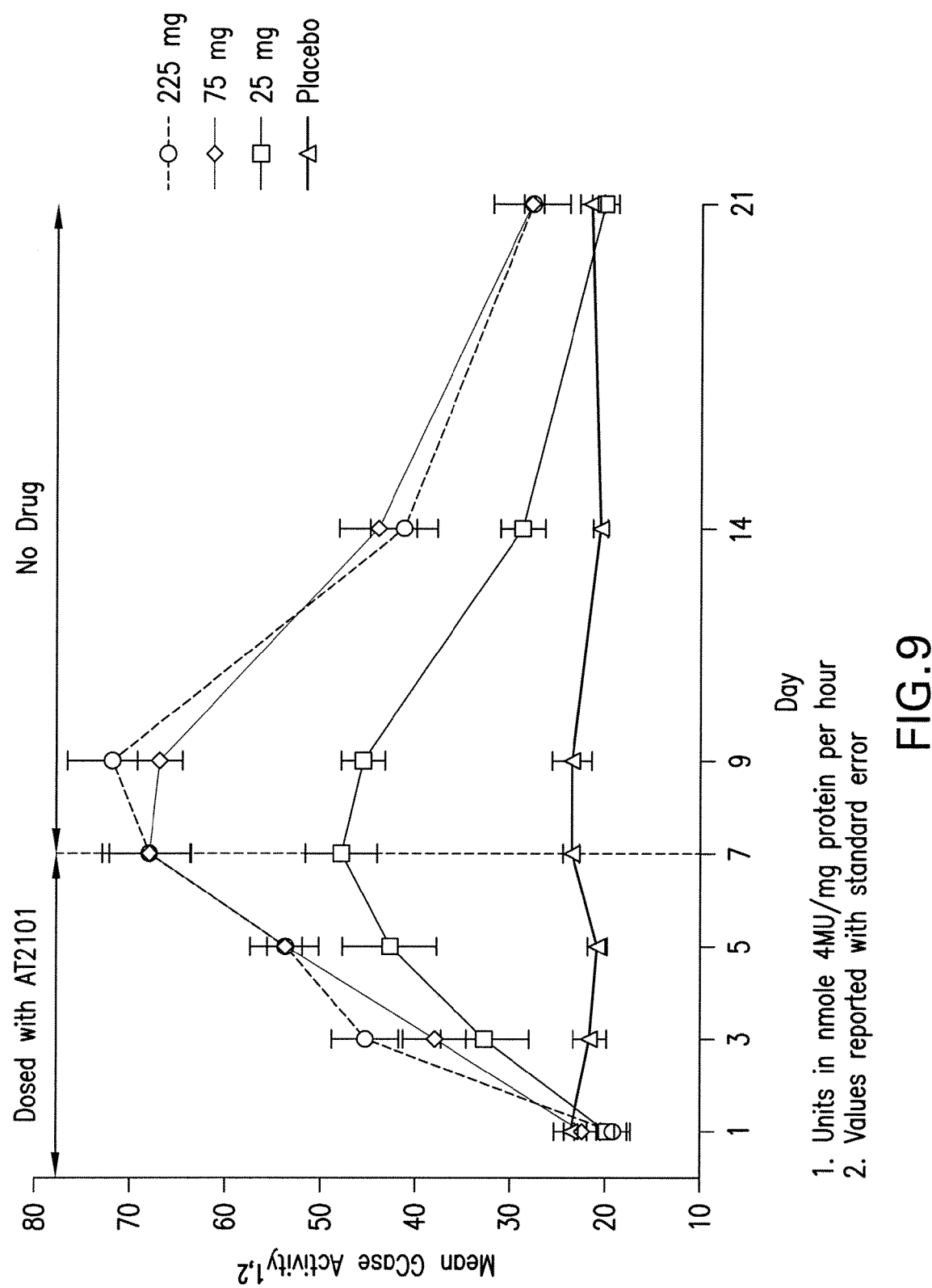
FIG. 9 shows Results of IFG tartrate on GCase activity of healthy individuals.
Figure 10:
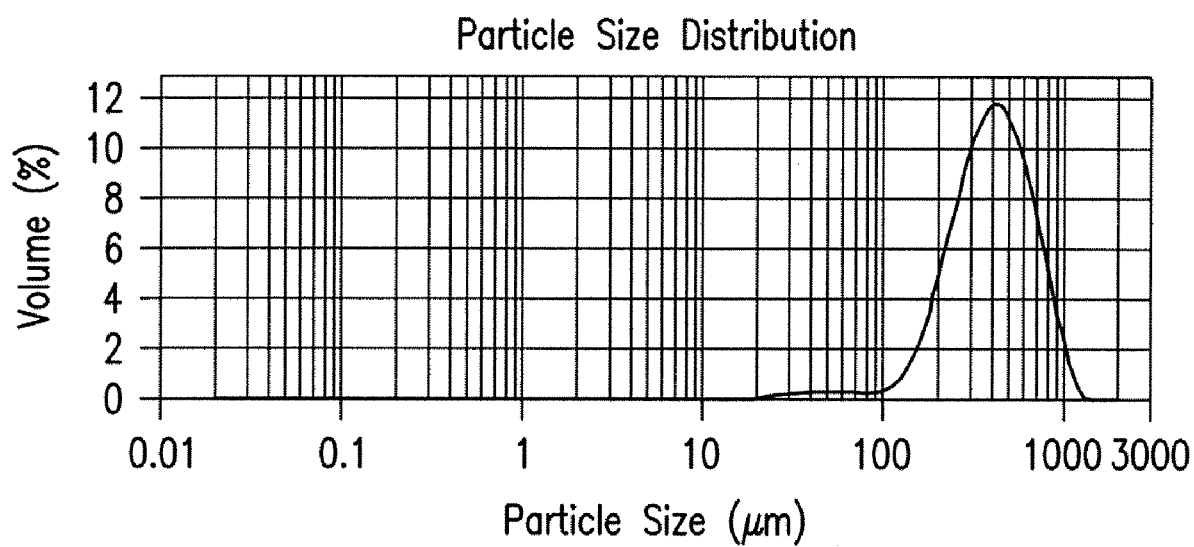
FIG. 10 shows a particle size distribution analysis result of isofagomine prepared according to one embodiment of the present invention.

In the multiple-dose study, GCase activity in isolated white blood cells was measured at days 1, 3, 5 and 7 during administration of isofagomine tartrate, and at days 9, 14 and 21 during the post-treatment washout period. In all subjects receiving isofagomine tartrate there was a marked increase in GCase levels during the treatment period, followed by a decrease upon removal of the drug and a return to near baseline levels by day 21 (FIG. 9). The increase in enzyme level was dose-related, reaching approximately 3.5-fold above baseline levels. These results for the safety, pharmacokinetics and preliminary pharmacodynamic effects in healthy volunteers support the further evaluation of isofagomine tartrate for the treatment of Gaucher disease.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A L-(+) tartaric acid salt of isofagomine represented by the structure:

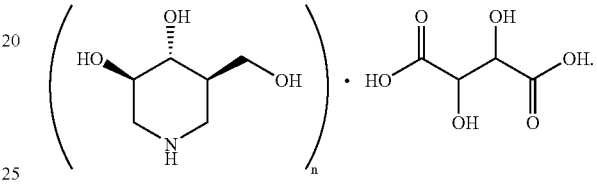

2. A pharmacuetical composition comprising the L-(+) tartaric acid salt of isofagomine of claim 1.

3. The pharmaceutical composition of claim 2, wherein the purity of the L-(+) tartaric acid salt of isofagomine present in the pharmaceutical composition is at least 98%.

4. The pharmaceutical composition of claim 2, wherein the purity of the L-(+) tartaric acid salt of isofagomine present in the pharmaceutical composition is at least 99%.

5. The pharmaceutical composition of claim 2, wherein the amount of L-(+) tartaric acid salt of isofagomine ranges from about 5 to about 300 mg per unit dose.

6. The pharmaceutical composition of claim 5, wherein the amount of L-(+) tartaric acid salt of isofagomine ranges from about 10 to about 100 mg per unit dose.

7. The pharmaceutical composition of claim 6 further comprising a pharmaceutically acceptable excipient.

8. A method of treating Gaucher disease comprising administering to an individual in need thereof an effective amount of the pharmaceutical composition as in any one of claims 2-7.

9. The method of claim 8 further comprising administering to the individual a functional glucocerebrosidase enzyme.

* * * * *